United States Patent [19]
Maginot

[11] Patent Number: 5,934,286
[45] Date of Patent: *Aug. 10, 1999

[54] BYPASS GRAFTING METHOD WHICH USES A NUMBER OF BALLOON CATHETERS TO INHIBIT BLOOD FLOW TO AN ANASTOMOSIS SITE

[75] Inventor: Thomas J. Maginot, Crown Point, Ind.

[73] Assignee: Maginot Vascular Systems, Crown Point, Ind.

[*] Notice: This patent is subject to a terminal disclaimer.

[21] Appl. No.: 09/090,598

[22] Filed: Jun. 4, 1998

Related U.S. Application Data

[63] Continuation of application No. 09/073,336, May 5, 1998, which is a continuation of application No. 08/702,742, Aug. 23, 1996, Pat. No. 5,749,375, which is a continuation of application No. 08/391,960, Feb. 21, 1995, Pat. No. 5,571,167, which is a continuation of application No. 08/138,912, Oct. 18, 1993, Pat. No. 5,456,712, which is a division of application No. 08/056,371, May 3, 1993, Pat. No. 5,304,220, which is a continuation-in-part of application No. 07/725,597, Jul. 3, 1991, Pat. No. 5,211,683.

[51] Int. Cl.$^6$ .................................................... A61B 17/08
[52] U.S. Cl. ................................. 128/898; 623/1; 604/8; 606/191; 606/153
[58] Field of Search ................................ 128/898; 623/1, 623/12; 606/153, 154, 155, 159, 191; 604/8

[56] References Cited

U.S. PATENT DOCUMENTS

| | | |
|---|---|---|
| 2,935,068 | 5/1960 | Donaldson . |
| 3,435,824 | 4/1969 | Gamponia ................................ 604/8 |
| 3,516,408 | 6/1970 | Montanti ................................ 604/8 |
| 3,657,744 | 4/1972 | Ersek . |
| 3,710,777 | 1/1973 | Sparks . |
| 3,818,511 | 6/1974 | Goldberg et al. . |
| 3,853,126 | 12/1974 | Schulte . |
| 3,866,247 | 2/1975 | Sparks ........................................ 623/1 |
| 3,908,663 | 9/1975 | Viek . |
| 4,061,134 | 12/1977 | Samuels et al. . |
| 4,183,102 | 1/1980 | Guiset . |
| 4,190,909 | 3/1980 | Ablaza . |
| 4,441,215 | 4/1984 | Kaster . |
| 4,447,227 | 5/1984 | Kotsanis .................................... 604/96 |
| 4,503,568 | 3/1985 | Madras . |
| 4,503,569 | 3/1985 | Dotter . |
| 4,546,499 | 10/1985 | Possis et al. . |
| 4,562,597 | 1/1986 | Possis et al. . |
| 4,617,932 | 10/1986 | Kornberg . |
| 4,655,771 | 4/1987 | Wallsten . |
| 4,743,251 | 5/1988 | Barra . |
| 4,769,029 | 9/1988 | Patel . |
| 4,776,337 | 10/1988 | Palmaz . |
| 4,787,899 | 11/1988 | Lazarus . |
| 4,795,458 | 1/1989 | Regan . |
| 4,830,003 | 5/1989 | Wolff et al. . |
| 4,856,516 | 8/1989 | Hillstead . |
| 4,872,874 | 10/1989 | Taheri . |
| 4,890,612 | 1/1990 | Kensey . |
| 4,892,539 | 1/1990 | Koch . |
| 4,929,246 | 5/1990 | Sinofsky . |
| 4,938,740 | 7/1990 | Melbin . |
| 4,954,126 | 9/1990 | Wallsten . |
| 4,957,508 | 9/1990 | Kaneko et al. . |
| 5,035,702 | 7/1991 | Taheri ...................................... 606/153 |
| 5,078,726 | 1/1992 | Kreamer . |
| 5,078,735 | 1/1992 | Mobin-Uddin . |
| 5,156,619 | 10/1992 | Ehrenfeld . |
| 5,211,683 | 5/1993 | Maginot ................................. 128/898 |
| 5,304,220 | 4/1994 | Maginot ..................................... 623/1 |
| 5,562,726 | 10/1996 | Chuter . |
| 5,571,167 | 11/1996 | Maginot ..................................... 623/1 |
| 5,749,375 | 5/1998 | Maginot ................................. 128/898 |

*Primary Examiner*—Paul B. Prebilic
*Attorney, Agent, or Firm*—Maginot, Addison & Moore

[57] ABSTRACT

A method of securing an end portion of a graft to a blood vessel of a patient's circulatory system during a bypass grafting procedure includes the step of inhibiting blood flow to a region of the circulatory system by inflating a number of balloons within the circulatory system, wherein a segment of the blood vessel is located in the blood flow inhibited region. The method further includes the step of creating an arteriotomy in a sidewall of the segment of the blood vessel while the number of balloons are inflated within the circulatory system. Additionally, the method includes the step of anastomosing the end portion of the graft to the segment of the blood vessel during the blood flow inhibiting step.

27 Claims, 27 Drawing Sheets

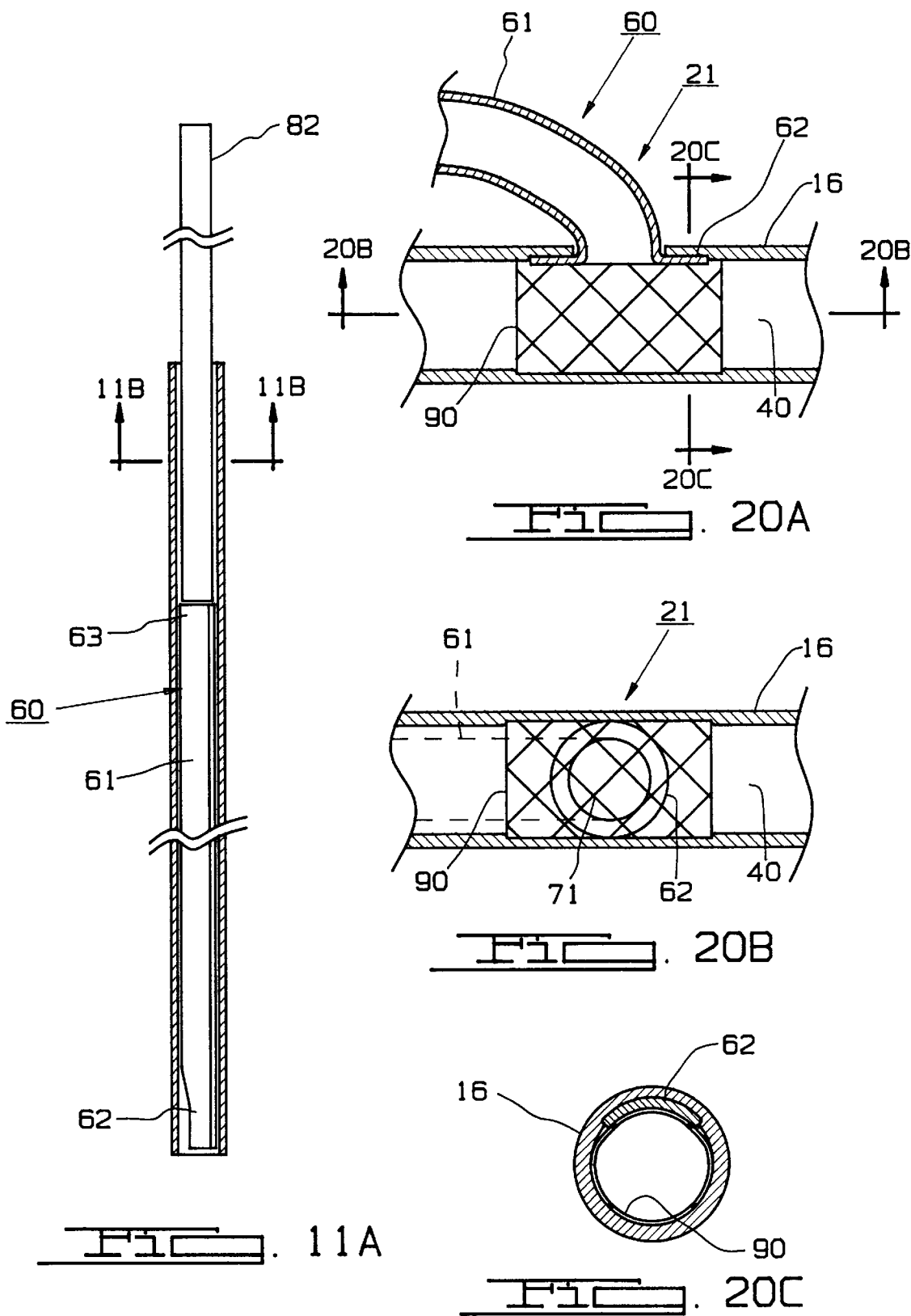

BYPASS GRAFTING METHOD WHICH USES A NUMBER OF BALLOON CATHETERS TO INHIBIT BLOOD FLOW TO AN ANASTOMOSIS SITE

This application is a continuation of application Ser. No. 09/073,336, filed May 5, 1998, which in turn is a continuation of application Ser. No. 08/702,742, filed Aug. 23, 1996, now U.S. Pat. No. 5,749,375, which in turn is a continuation of application Ser. No. 08/391,960, filed Feb. 21, 1995, now U.S. Pat. No. 5,571,167, which is in turn a continuation of application Ser. No. 08/138,912, filed Oct. 18, 1993, now U.S. Pat. No. 5,456,712, which is in turn a division of application Ser. No. 08/056,371, filed on May 3, 1993, now U.S. Pat. No. 5,304,220, which in turn is a continuation-in-part of application Ser. No. 07/725,597, filed on Jul. 3, 1991, now U.S. Pat. No. 5,211,683.

BACKGROUND OF THE INVENTION

The present invention relates generally to a method for improving blood flow in the body of a patient and more particularly concerns a bypass grafting method which uses a number of balloon catheters to inhibit blood flow to an anastomosis site.

Treatment of vascular disease in which the lumen of a blood vessel is significantly narrowed or occluded by atherosclerosis includes surgical and endovascular methods. Conventional surgical methods include obtaining access to a blood vessel via one or more surgical incisions and either removing the blockage by performing an endarterectomy or bypassing the blockage by placing a bypass graft which has a generally cylindrical shape. Endovascular methods include obtaining access to a blood vessel with a catheter and improving blood flow therein by performing an athrectomy, atherolysis, or balloon and laser angioplasty with or without endovascular stent placement. In general, the preferred treatment of severe stenosis or occlusion of a long vessel segment has been surgical bypass grafting.

Although conventional surgical bypass grafting is an accepted procedure, it presents substantial morbidity and mortality risks. Also, not all patients are acceptable candidates for the above surgical procedure due to advanced age and preexisting medical conditions. Moreover, conventional surgical bypass grafting is an invasive procedure which may require extended hospitalization due to postoperative recovery. In addition, the above surgical procedure may involve substantial financial costs to patients, hospitals and society in general. Further, incisions made during the above surgical procedure may cause significant cosmetically unattractive scarring which is undesirable to many patients.

SUMMARY OF THE INVENTION

One embodiment of the present invention involves a method of implanting a graft prosthesis in the body of a patient to bypass a segment of a blood vessel. The method includes the steps of (1) making an incision in the body, (2) positioning a graft so that one end of the graft is located substantially adjacent the blood vessel at a site upstream of the segment and a second end of the graft is located substantially adjacent the blood vessel at a site downstream of the segment, wherein the positioning step includes the step of placing the graft into the body through the incision, and further wherein the positioning step is performed while the upstream site is covered by a substantially intact portion of the epidermis of the body, (3) isolating a region of the area within the blood vessel substantially adjacent the upstream site from fluid communication with the rest of the area within the blood vessel, wherein the upstream isolating step is performed while the upstream site is covered by the substantially intact portion of the epidermis of the body, (4) making an arteriotomy in a sidewall of the blood vessel substantially adjacent the upstream site to create a communicating aperture between the upstream isolated region and an area outside of the blood vessel, wherein the upstream arteriotomy making step is performed while the upstream site is covered by the substantially intact portion of the epidermis of the body, (5) forming an anastomosis between the one end of the graft and the blood vessel substantially adjacent the upstream site, wherein the upstream anastomosis forming step is performed while the upstream site is covered by the substantially intact portion of the epidermis of the body, and further wherein the upstream anastomosis forming step includes the step of suturing the one end of the graft to the blood vessel, (6) isolating a region of the area within the blood vessel substantially adjacent the downstream site from fluid communication with the rest of the area in the blood vessel, (7) making an arteriotomy in the sidewall of the blood vessel substantially adjacent the downstream site to create a communicating aperture between the downstream isolated region and the area outside of the blood vessel, and (8) forming an anastomosis between the second end of the graft and the blood vessel substantially adjacent the downstream site.

Another embodiment of the present invention involves a method for implanting an end portion of a graft within the body of a patient during a bypass grafting procedure. The method includes the steps of (1) making an incision in the body at a first location, (2) isolating a region of the area within a blood vessel of the body substantially adjacent a second location from fluid communication with the rest of the area within the blood vessel, wherein the first location is remote from the second location, and further wherein the isolating step is performed while the second location is covered by a substantially intact portion of the epidermis of the body, (3) making an arteriotomy in the sidewall of the blood vessel substantially adjacent the second location to create a communicating aperture between the isolated region and the outside of the blood vessel, wherein the arteriotomy making step is performed while the second location is covered by the substantially intact portion of the epidermis of the body, (4) advancing the end portion of the graft through the incision to the second location, wherein the advancing step is performed while the second location is covered by the substantially intact portion of the epidermis of the body, and (5) forming an anastomosis between the end portion of the graft and the blood vessel substantially adjacent the second location, wherein the anastomosis forming step is performed while the second location is covered by the substantially intact portion of the epidermis of the body, and further wherein the anastomosis forming step includes the step of suturing the end portion of the graft to the blood vessel.

Still another embodiment of the present invention involves a graft which is securable to a sidewall of a blood vessel having an arteriotomy defined therein. The graft includes a body portion, and a flanged end portion attached to the body portion, the flanged end portion being positionable substantially adjacent a portion of the sidewall of the blood vessel which substantially surrounds the arteriotomy.

Yet another embodiment of the present invention involves a graft and stent assembly which is securable to a sidewall of a blood vessel having an arteriotomy defined therein. The graft and stent assembly includes a graft having an end portion which is positionable within the blood vessel and substantially adjacent a portion of the sidewall of the blood vessel which substantially surrounds the arteriotomy. The graft and stent assembly further includes a stent positionable within the blood vessel and in contact with the end portion of the graft so as to secure the end portion of the graft between the sidewall of the blood vessel and the stent.

One object of the present invention is to provide an improved method for implanting a graft prosthesis in the body of a patient.

Another object of the present invention is to provide an improved method for implanting an end portion of a graft within the body of a patient.

Still another object of the present invention is to provide a method of implanting a graft prosthesis in the body of a patient which is less invasive relative to conventional surgical bypass grafting procedures.

Yet another object of the present invention is to provide a method of implanting a graft prosthesis in the body of a patient which obviates at least one surgical incision (e.g. the abdominal surgical incision) as compared to conventional surgical bypass grafting procedures.

Still another object of the present invention is to provide a method of implanting a graft prosthesis in the body of a patient which has low morbidity and mortality risk to patients.

Yet another object of the present invention is to provide a method of implanting a graft prosthesis in the body of a patient which can be performed on patients whom are elderly or have poor preexisting medical conditions.

Still another object of the present invention is to provide a method of implanting a graft prosthesis in the body of a patient which requires relatively less financial costs to patients, hospitals and society in general as compared to conventional surgical bypass grafting techniques.

Yet another object of the present invention is to provide an improved graft prosthesis.

Still another object of the present invention is to provide an improved graft and stent assembly.

Another object of the present invention is to provide a graft which can be conveniently secured to a blood vessel.

Yet another object of the present invention is to provide a graft and stent assembly which allows the graft to be conveniently secured to a blood vessel.

Yet still another object of the present invention is to provide a graft which is easy to implant in the body of a patient.

Still another object of the present invention is to provide a graft and stent assembly which is easy to implant in the body of a patient.

Another object of the present invention is to provide a graft which functions well after it is implanted in the body of a patient.

Yet another object of the present invention is to provide a graft and stent assembly which functions well after it is implanted in the body of a patient.

Other objects and benefits of the present invention can be discerned from the following description and accompanying drawings.

BRIEF DESCRIPTION OF THE DRAWINGS

FIG. 1 also shows a portion of each inguinal ligament of the human body.

FIG. 11A is an elevational view of the laparoscope of FIG. 6. Moreover, FIG. 11A shows the graft prosthesis of FIG. 10A, positioned within the laparoscope in accordance with the method of the present invention. FIG. 11A further shows a plunger, used in carrying out the preferred method of the present invention, partially positioned within the laparoscope in accordance with the preferred method of the present invention.

FIG. 20A is an enlarged side elevational view showing the anastomosis of FIG. 19A.

FIG. 20B is a cross-sectional view taken along the line 20B—20B of FIG. 20A as viewed in the direction of the arrows.

FIG. 20C is a cross-sectional view taken along the line 20C—20C of FIG. 20A as viewed in the direction of the arrows.

DESCRIPTION OF THE PREFERRED EMBODIMENT

Figure 1:
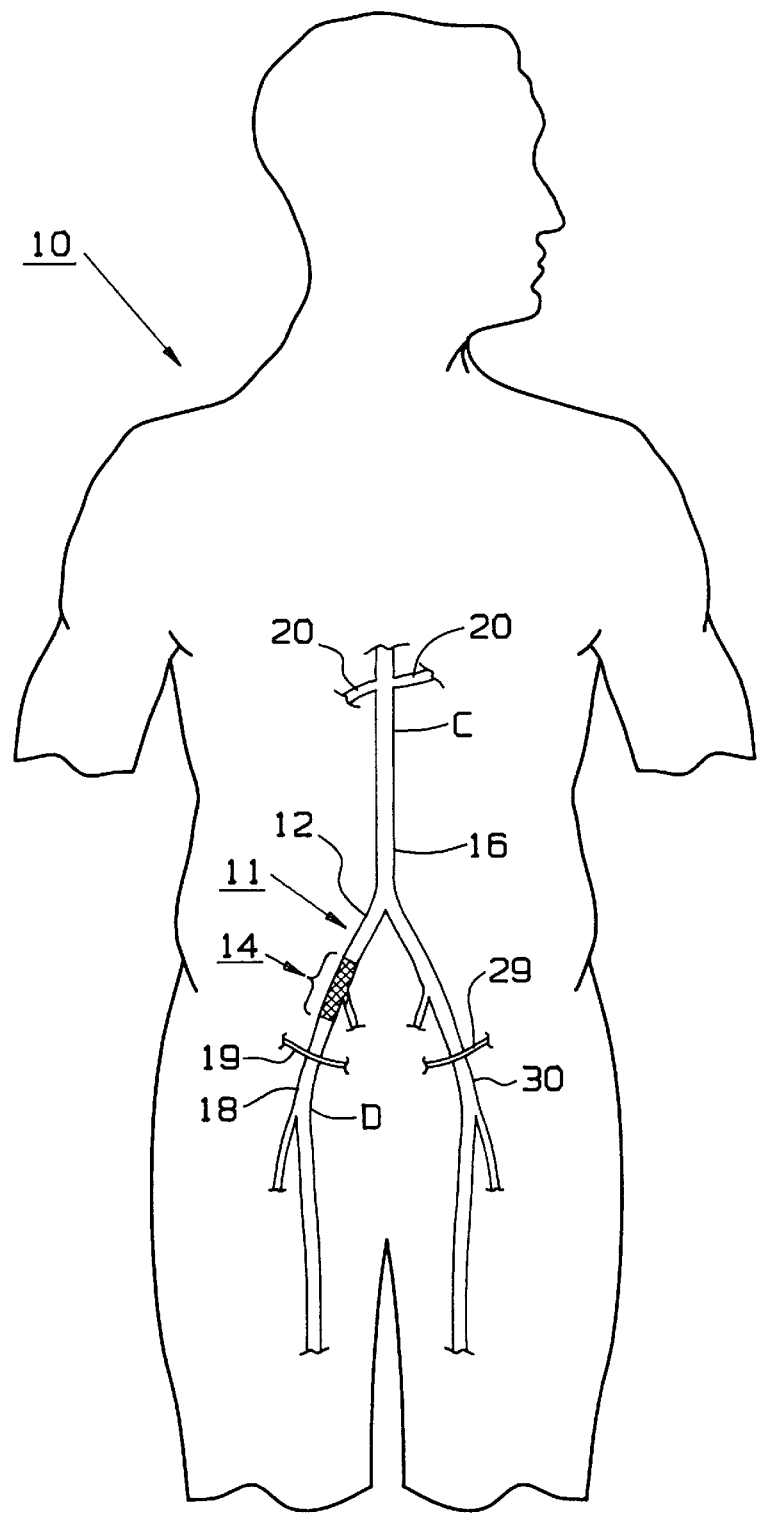
FIG. 1 is a fragmentary front elevational view of a human body showing a blood vessel which includes the aorta, the right common iliac artery, the right common femoral artery and the left common femoral artery wherein a segment of the blood vessel is occluded.

For the purposes of promoting an understanding of the principles of the invention, reference will now be made to the embodiments and methods illustrated in the drawings and specific language will be used to describe the same. It will nevertheless be understood that no limitation of the scope of the invention is thereby intended, such alterations and further modifications in the illustrated devices and methods, and such further applications of the principles of the invention as illustrated therein being contemplated as would normally occur to one skilled in the art to which the invention relates.

Figure 2:
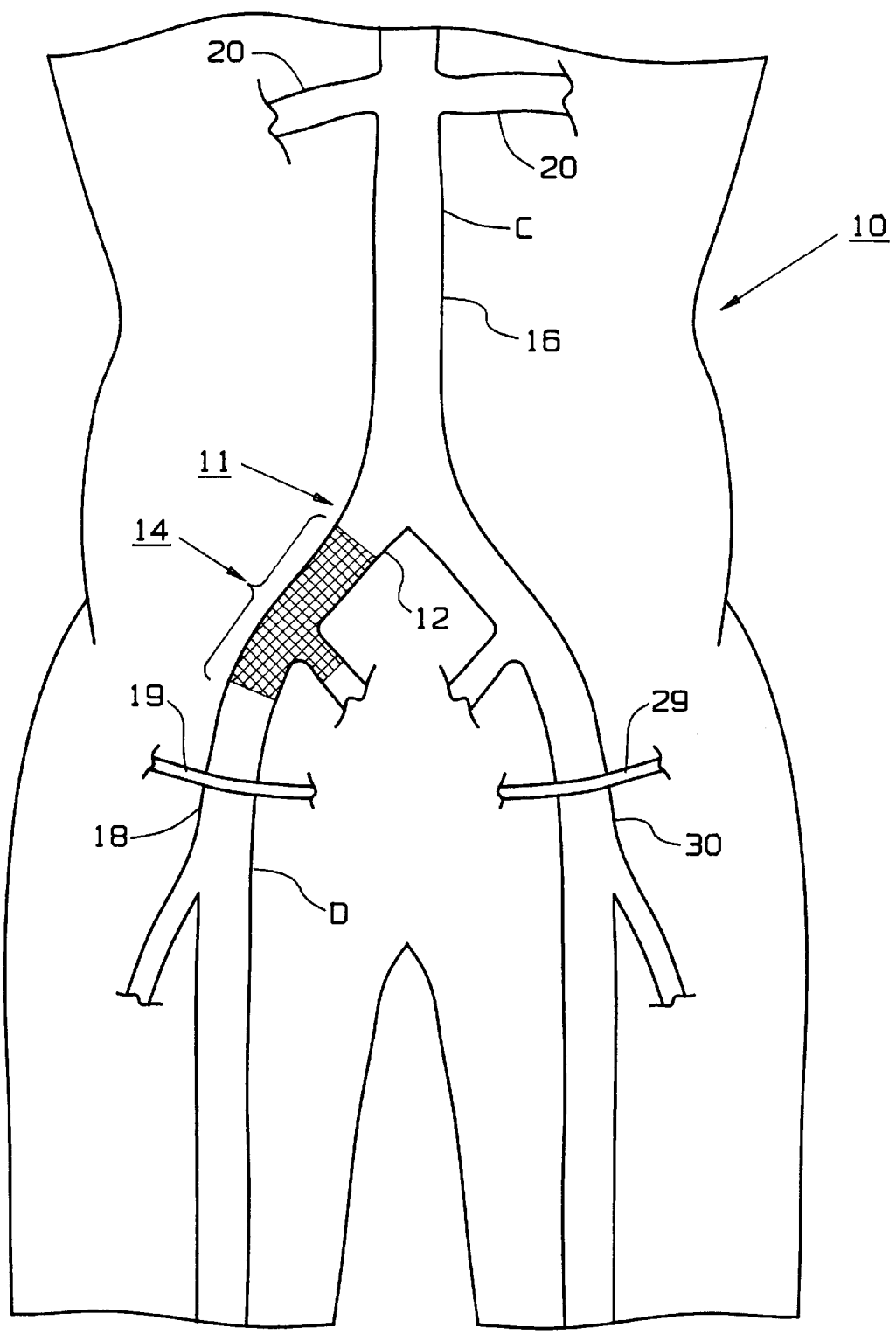
FIG. 2 is an enlarged fragmentary view of the human body and blood vessel of FIG. 1.

Referring now to the drawings, FIG. 1shows a portion of a human body, generally designated by the reference numeral 10, with an artery, the common iliac artery 12, having an occluded segment, generally designated by the reference numeral 14. Human body 10 is further shown having other arteries, in particular, aorta 16, right common femoral artery 18, left common femoral artery 30 and renal arteries 20. In addition, human body 10 includes a right inguinal ligament 19 and a left inguinal ligament 29. Human body 10 also includes an epidermis 13 (see e.g. FIG. 6). The preferred method disclosed herein describes the implantation of a graft to couple aorta 16 to right common femoral artery 18 thereby bypassing occluded segment 14. FIG. 2 shows an enlarged view of aorta 16, right common iliac artery 12, occluded segment 14, right common femoral artery 18, left common femoral artery 30, renal arteries 20 and right inguinal ligament 19. In FIGS. 1 and 2, a blood vessel is shown, generally designated by the reference numeral 11, which includes aorta 16, right common iliac artery 12, right common femoral artery 18 and left common femoral artery 30. Blood vessel 11, when not occluded, conveys blood from a point C within aorta 16 to a point D within right common femoral artery 18 (see FIGS. 1–2). However, due to the presence of occluded segment 14, blood is substantially totally precluded from being conveyed from point C within aorta 16 to point D within right common femoral artery 18 via the direct route of right common iliac artery 12. While the inventive method will hereinafter be described with regard to a substantially totally occluded segment of a blood vessel of a patient, it will be understood to one skilled in the art that the inventive method is equally effective for bypass of a partially occluded segment of a blood vessel. In addition, the inventive method is also useful for bypass of an aneurysmal segment of a blood vessel.

Referring now to FIGS. 3–24, successive steps according to the preferred method of the present invention are depicted of the implantation of a graft prosthesis of the present invention to couple aorta 16 to right common femoral artery 18 thereby bypassing occluded segment 14 of blood vessel 11.

One step of the preferred method of the present invention comprises isolating a region of the area within the blood vessel 11, located near a site 21 (see FIG. 4) upstream of occluded segment 14, from fluid communication with the rest of the area within the blood vessel. There also exists a site 31 which is located downstream of occluded segment 14 (see FIG. 4). Upstream site 21is located substantially adjacent the blood vessel 11 and designates a working area where the distal end of medical instruments and various medical devices may be positioned during the process of securing one end of a graft to the blood vessel. Upstream site 21 is located near blood vessel 11 so as to allow such distal end of medical instruments and medical devices to be appropriately manipulated at upstream site 21 to thereby successfully secure the one end of the graft to the blood vessel. Downstream site 31 is located substantially adjacent the blood vessel 11 and also designates a working area where the distal end of medical instruments, physician's hands and various medical devices may be positioned during the process of securing a second end of the graft to the blood vessel. Downstream site 31 is also located near blood vessel 11 so as to allow such distal end of medical instruments, physician's hands and medical devices to be appropriately manipulated at downstream site 31 to thereby successfully secure the second end of the graft to the blood vessel.

Figure 3:
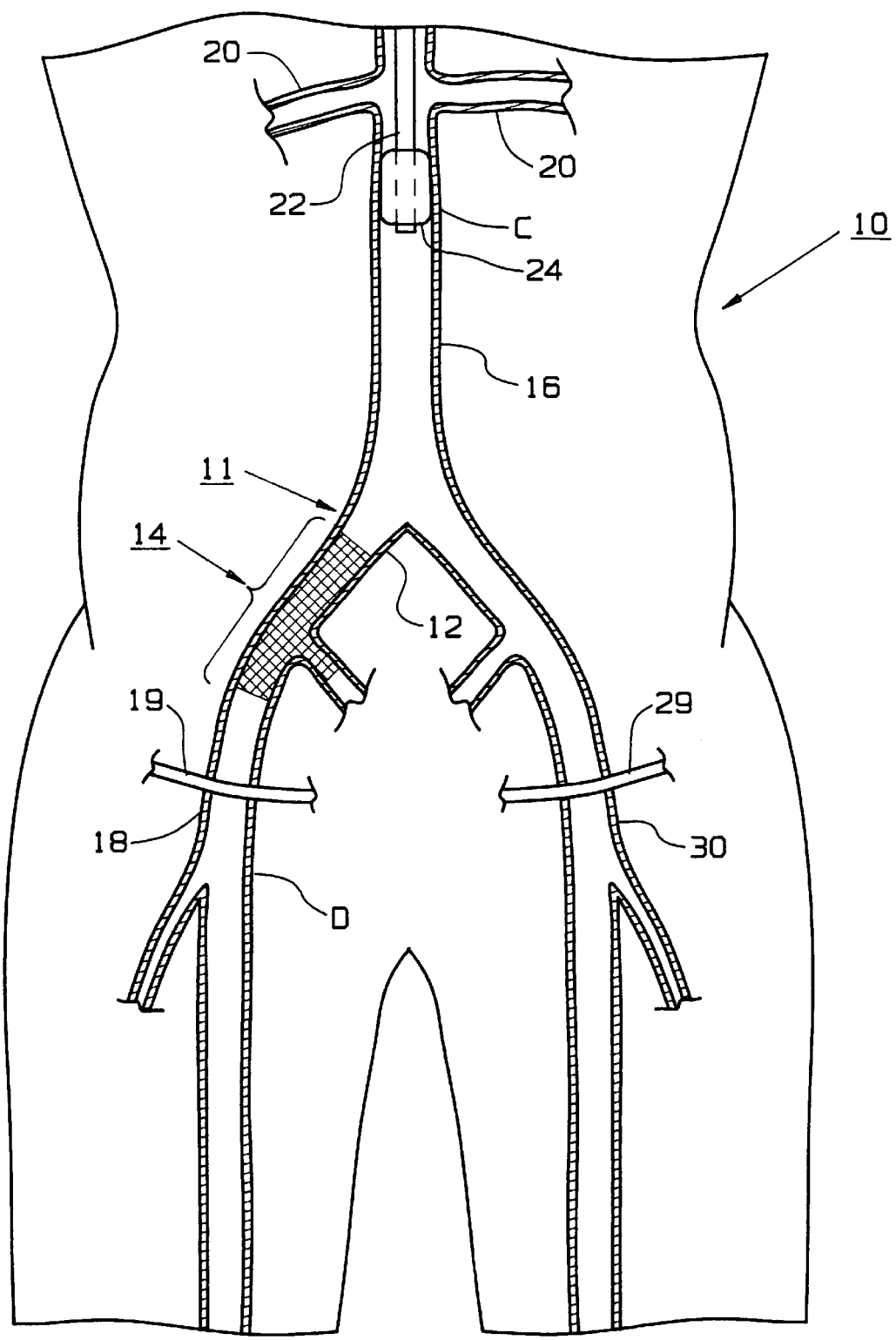
FIG. 3 shows the human body and blood vessel of FIG. 2 with a balloon-tip catheter positioned within the blood vessel wherein the balloon is inflated in accordance with the preferred method of the present invention.

Referring now to FIG. 3, a balloon-tip catheter 22 having a balloon 24 thereon is percutaneously inserted into blood vessel 11 via the right or left axillary artery (not shown). This step may be accomplished using standard catherization techniques. The distal end of catheter 22 is then advanced into aorta 16 until balloon 24 is positioned distal to renal arteries 20 as shown in FIG. 3. Balloon 24 is then inflated to and maintained at a size such that fluid communication is substantially terminated in aorta 16 between the portion of blood vessel 11 proximal to balloon 24 and the portion of blood vessel 11 distal to balloon 24. Since conventional balloon-tip catheters may not have a balloon thereon that possess the characteristics necessary to terminate fluid communication in the aorta as described above, modification may be readily made to an existing design of a conventional balloon-tip catheter to achieve the above desired results. One such modification would include providing a balloon on the catheter with is inflatable to an outer diameter which is larger than the inner diameter of the aorta. Another such modification would include providing a coarse textured outer surface to the balloon of the catheter. The above modification would provide increased frictional resistance between the inflated balloon and the sidewall of the blood vessel when force is applied to the balloon in the axial direction thereof. A balloon-tip catheter having a conventional design is available through Medi-tech, Incorporated of Watertown, Mass., as Order No. 17-207 (Description: OBW/40/8/2/100).

Figure 4:
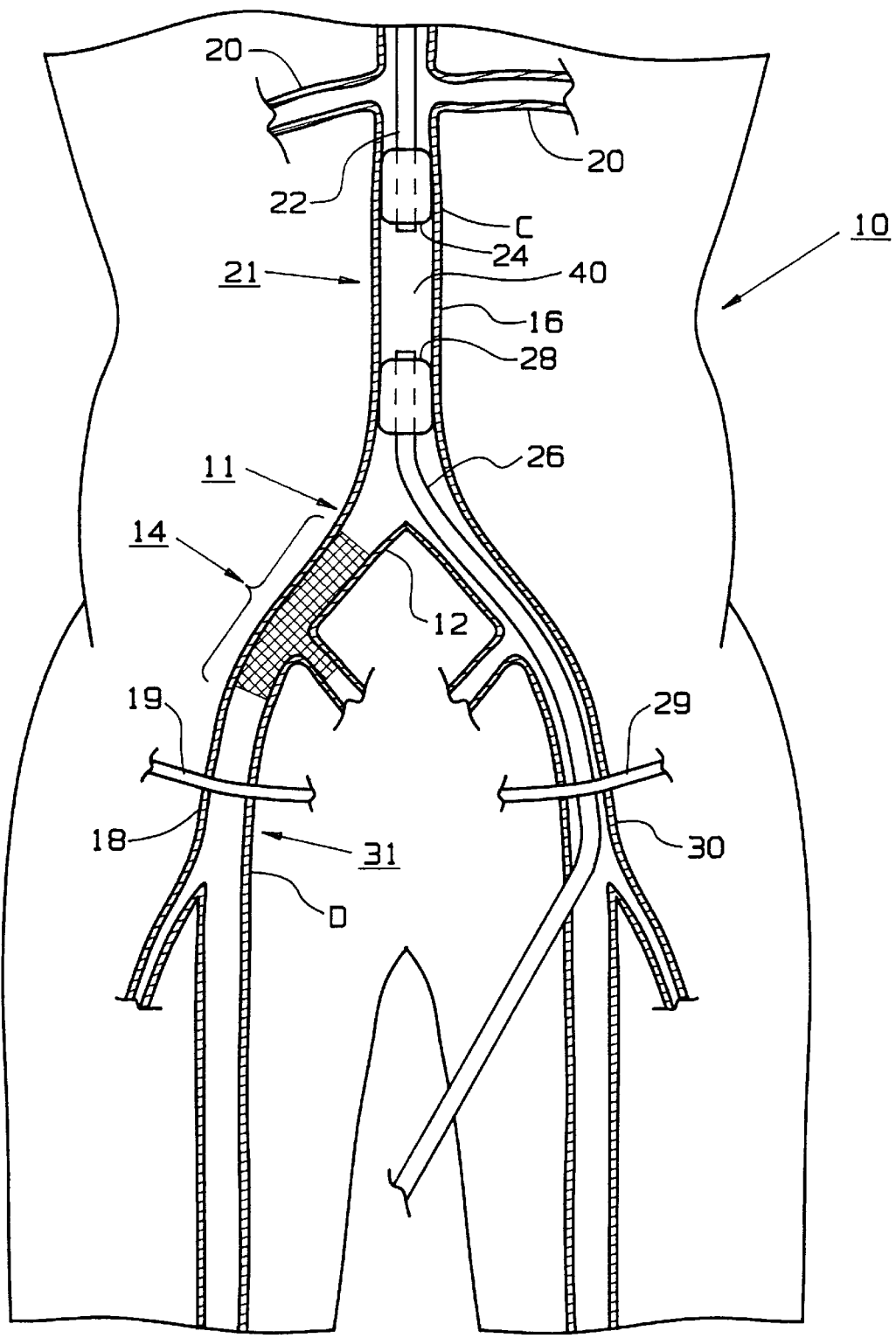
FIG. 4 is a view similar to FIG. 3 but showing a second balloon-tip catheter positioned within the blood vessel wherein the second balloon is inflated in accordance with the preferred method of the present invention.

Referring now to FIG. 4, a balloon-tip catheter 26 having a balloon 28 thereon and an open lumen defined therein is percutaneously inserted into blood vessel 11 via the left common femoral artery 30. This step may be accomplished using standard catherization techniques. The distal end of the catheter 26 is then advanced into aorta 16 until balloon 28 is positioned proximal to the aortic bifurcation. Balloon 28 is then inflated to and maintained at a size such that fluid communication is substantially terminated in aorta 16 between the portion of blood vessel 11 proximal to balloon 28 and the portion of blood vessel 11 distal to balloon 28. Since conventional balloon-tip catheters may not have a balloon thereon that possess the characteristics necessary to terminate fluid communication in the aorta as described above, modification similar to that described with respect to catheter 22 may need to be made to catheter 26. In addition, further modification may need to be made to catheter 26 since a conventional balloon-tip catheter may not have an open central lumen defined therein which possesses a diameter large enough for the advancement therethrough of a compressed stent mounted on a balloon of another balloon-tip catheter as will be required by the preferred method of the present invention (see FIG. 17). Such further modification would be to create an open central lumen in catheter 26 that possesses a diameter larger than the outer diameter of the compressed stent which is mounted on the balloon of the balloon-tip catheter as referred to above. Due to the increased size requirements of catheter 26 as alluded to above, a surgical cut-down may need to be performed in order to expose left common femoral artery 30. Such exposure would facilitate both placement of catheter 26 into blood vessel 11 and repair of such blood vessel following subsequent removal of such catheter therefrom.

Temporary occlusion of the blood flow in the inferior mesenteric artery (not shown) by laparoscopic procedures may need to be performed in order to prevent the flow of blood from the inferior mesenteric artery into aorta 16 due to placement of inflated balloons 24 and 28 as discussed above.

The region bound by balloon 24 of catheter 22 and balloon 28 of catheter 26 and the sidewall of blood vessel 11 contained therebetween defines a region 40 of the area within blood vessel 11, located near site 21 upstream of occluded segment 14, which is substantially isolated from fluid communication with the rest of the area within blood vessel 11.

Alternatively, the step of isolating the region of the area within blood vessel 11, located near upstream site 21, from fluid communication with the rest of the area within the blood vessel may be accomplished by laparoscopically placing a first clamp around the blood vessel 11 at the location where balloon 24 of the balloon-tip catheter 22 was described as having been inflated and also laparoscopically placing a second clamp around the blood vessel 11 at the location where balloon 28 of the balloon-tip catheter 26 was described as having been inflated.

Another step according to the method of the present invention comprises making an arteriotomy in the sidewall of blood vessel 11, near upstream site 21, to create a communicating aperture between upstream isolated region 40 and the outside of blood vessel 11.

Figure 5:
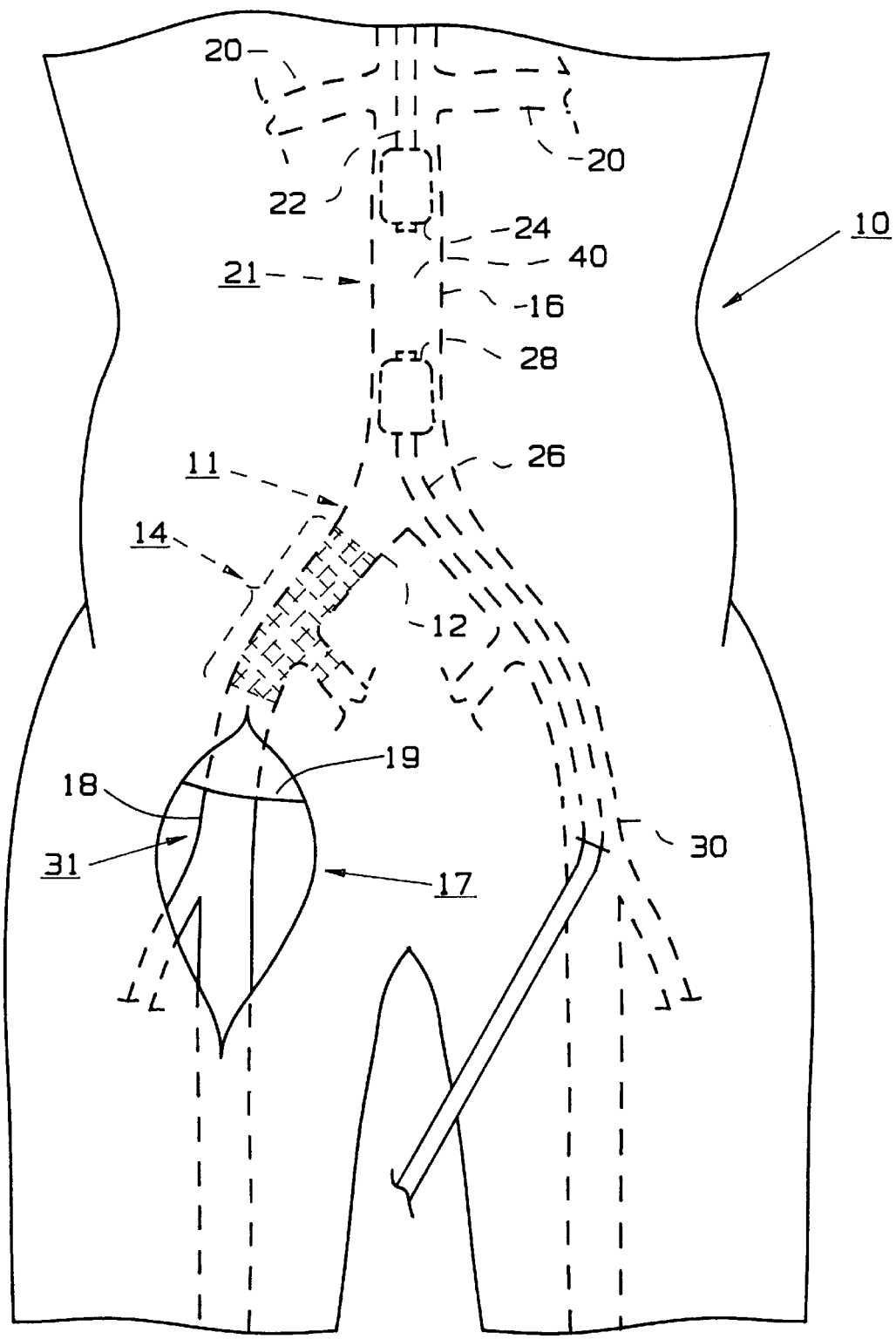
FIG. 5 is a view similar to FIG. 4 but showing the blood vessel in phantom except for a portion thereof that is exposed through a gaping surgical incision. Also shown exposed through the surgical incision in FIG. 5 is a portion of the right inguinal ligament.

Referring now to FIG. 5, right common femoral artery 18 and right inguinal ligament 19 are exposed via a surgical incision 17. Such exposure is accomplished using standard surgical techniques.

Figure 6:
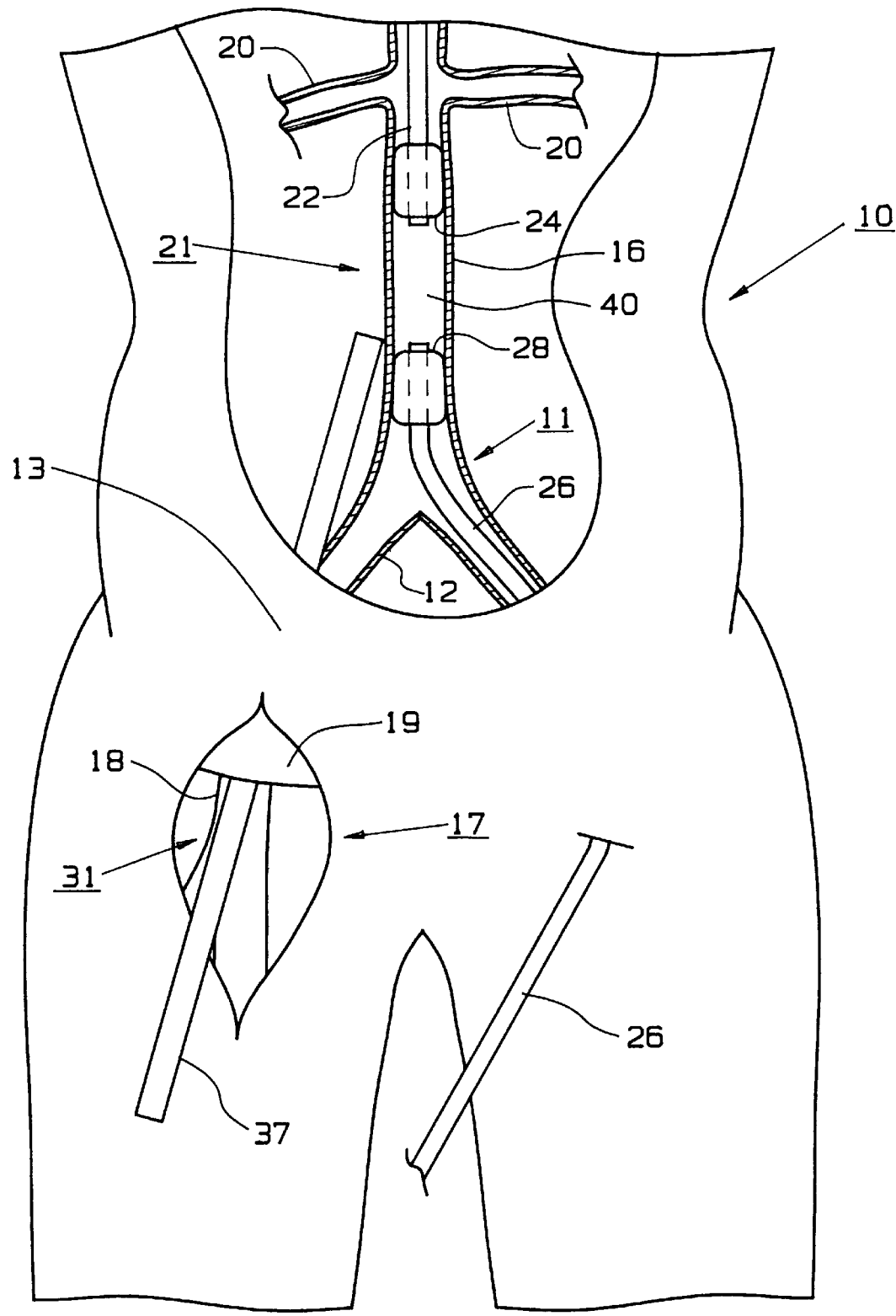
FIG. 6 is a view similar to FIG. 5 but showing another portion of the blood vessel, including the aorta, exposed for clarity of description. Moreover, in FIG. 6, a laparoscope (depicted schematically) is shown inserted through the surgical incision in accordance with the preferred method of the present invention.

Insufflation of the peritoneal cavity is then performed using standard techniques associated with laparoscopy. A laparoscope 37 (see FIG. 6), having an open central lumen (i.e. a working channel) defined therein, is then inserted into human body 10 through the opening between right common femoral artery 18 and right inguinal ligament 19. Laparoscope 37 may additionally include a fiber optic illumination device and a telescope for viewing. A tilt table may be used with the patient (i.e. human body 10) positioned thereon in order to maneuver the patient's abdominal contents away from the laparoscope insertion site and the area near upstream site 21. Laparoscope 37 is then advanced toward upstream site 21 until its distal end is positioned thereat as shown in FIG. 6. One or more additional laparoscopes and associated laparoscopic operating instruments may be employed using standard laparoscopic techniques to assist in the above positioning via direct visualization, tissue retraction and tissue dissection. One laparoscope which may be used in carrying out the preferred method of the present invention is available through Karl Storz Endoscopy-America, Incorporated of Culver City, Calif. as Catalog No. 26075A. Modification may be readily made to laparoscope 37, such as rounding the distal edge thereof, in order to reduce the possibility of tissue trauma as a result of advancement of laparoscope 37 within human body 10. A book which discloses various standard laparoscopic techniques and standard associated laparoscopic operating instruments is entitled "Laparoscopy for Surgeons," authored by Barry A. Salky, M.D., published by Igaku-Shoin Medical Publishers, Inc. of New York, N.Y., U.S.A. (1990), and the pertinent part of the disclosure of which is herein incorporated by reference.

Figure 7:
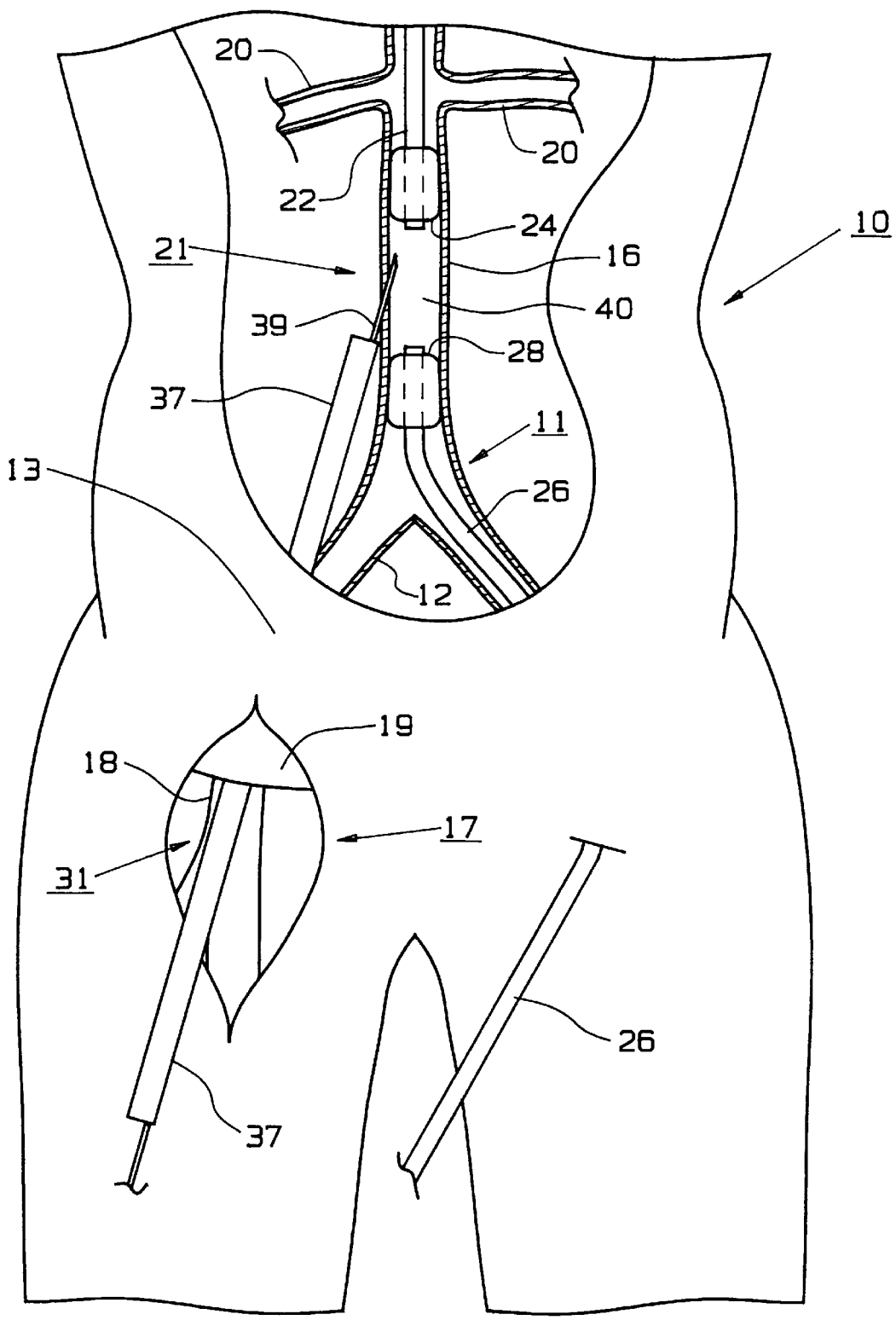
FIG. 7 is a view similar to FIG. 6 but showing a needle positioned within the laparoscope in accordance with the preferred method of the present invention.
Figure 8:
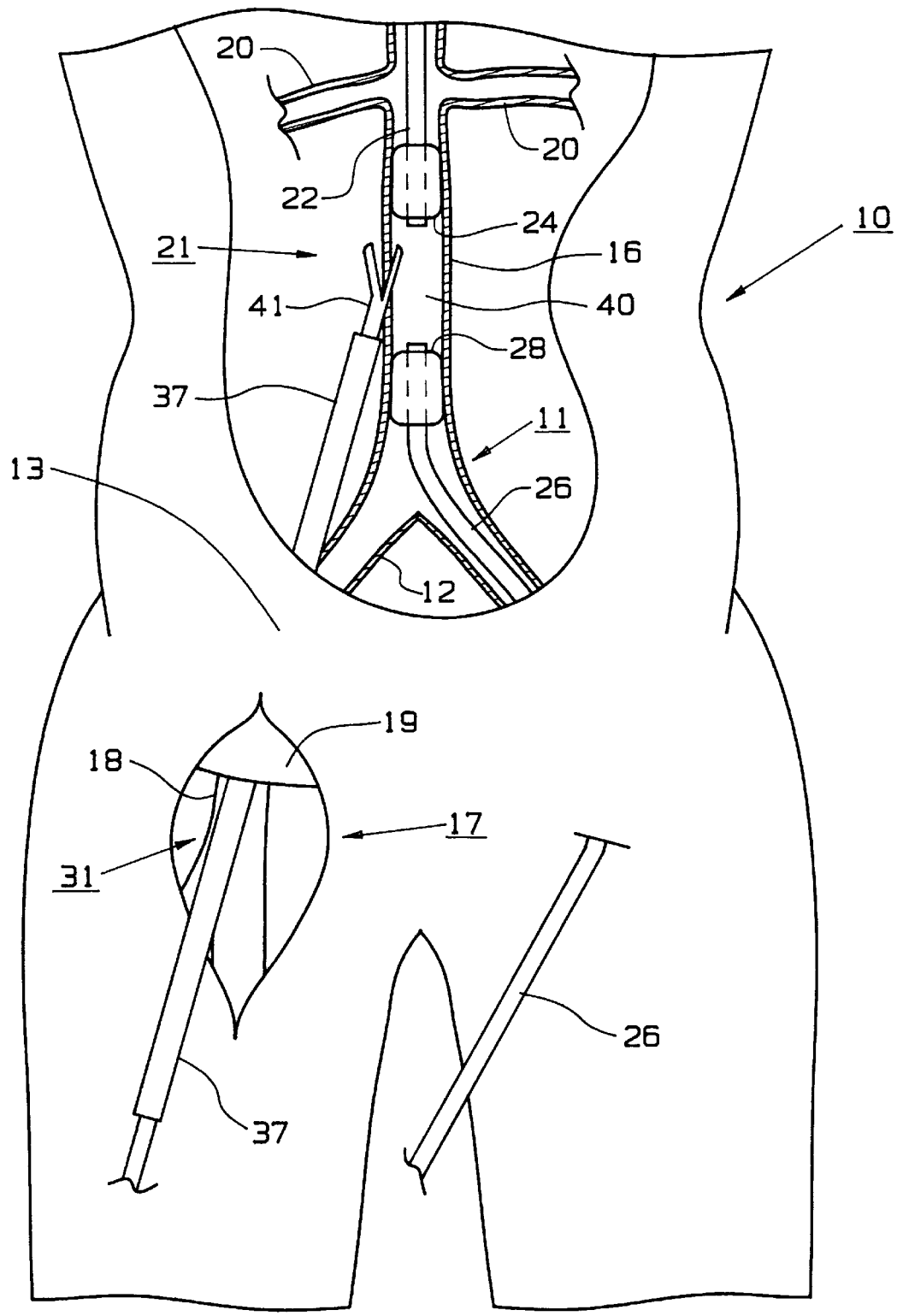
FIG. 8 is a view similar to FIG. 7 but showing the needle removed from the laparoscope and replaced with a scissors device in accordance with the preferred method of the present invention.

Referring now to FIG. 7, a puncture needle 39 is advanced through the open central lumen of laparoscope 37 until its distal end exits the laparoscope. Thereafter, needle 39 is manipulated to penetrate through the sidewall of blood vessel 11 to the inside thereof, thus creating a puncture in the blood vessel. Needle 39 is then withdrawn and a scissors device 41 is advanced through the open central lumen of laparoscope 37 until its distal end exits the laparoscope (see FIG. 8). The scissors device is then manipulated to enlarge the puncture in the sidewall of the blood vessel. Scissors device 41 is then withdrawn from laparoscope 37. One puncture needle which may be used in carrying out the preferred method of the present invention is available through Karl Storz Endoscopy-America, Incorporated of Culver City, Calif., as Catalog No. 26178R. Additionally, one scissors device which may be used in carrying out the method of the present invention is available through Karl Storz Endoscopy-America, Incorporated of Culver City, Calif., as Catalog No. 26178PS.

It should be noted that if upstream isolated region 40 was not substantially isolated from fluid communication with the rest of the area within the blood vessel, the act of making an arteriotomy in the sidewall of blood vessel 11 near upstream site 21 would cause significant blood leakage out of blood vessel 11 and such blood leakage may be fatal to the patient.

According to another step of the method of the present invention, a graft prosthesis is positioned so that one end of the graft is located substantially adjacent blood vessel 11 at downstream site 21 and the other end of the graft prosthesis is located substantially adjacent blood vessel 11 at downstream site 31. The above positioning step includes the step of advancing the graft prosthesis within the human body 10 with a medical instrument.

Figure 9A:
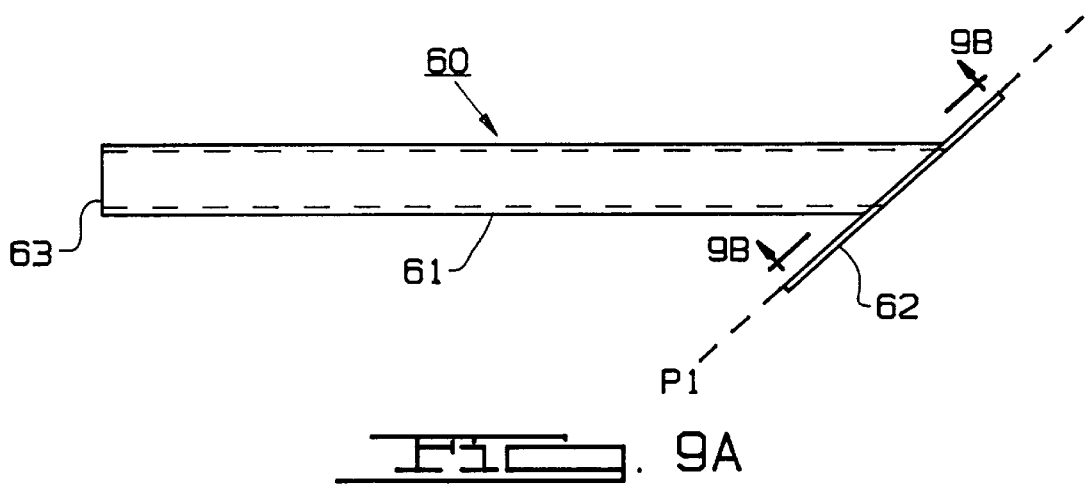
FIG. 9A is an elevational view of a graft prosthesis used in carrying out the preferred method of the present invention.
Figure 9B:
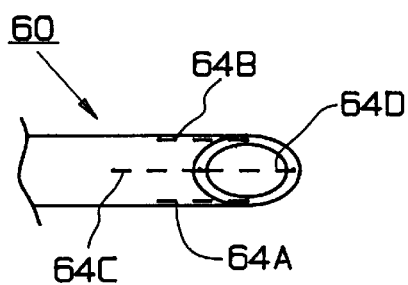
FIG. 9B is a fragmentary sectional view taken along the line 9B—9B of FIG. 9A as viewed in the direction of the arrows.
Figure 9C:
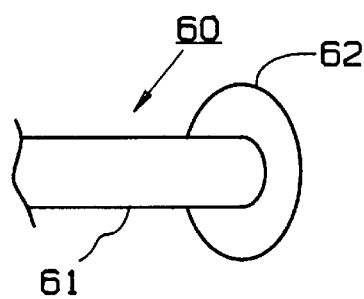
FIG. 9C is a fragmentary perspective view of the graft prosthesis of FIG. 9A showing its outwardly extending flanged end portion.
Figure 9D:
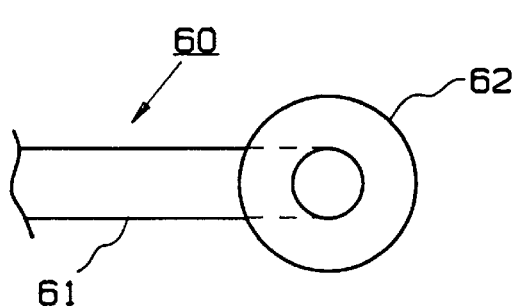
FIG. 9D is another fragmentary perspective view of the graft prosthesis of FIG. 9A showing its outwardly extending flanged end portion.
Figure 9E:
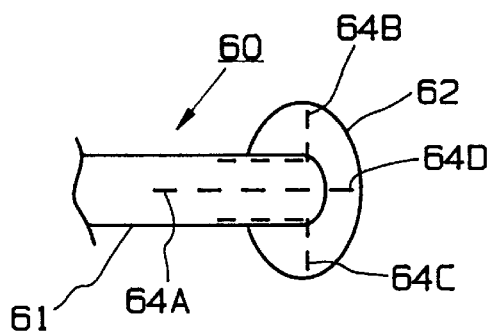
FIG. 9E is a view similar to FIG. 9C but showing a plurality of springs, in phantom, integrally positioned within the outwardly extending flanged end portion, in addition to, a portion of the sidewalls of the graft prosthesis of FIG. 9A.
Figure 9F:
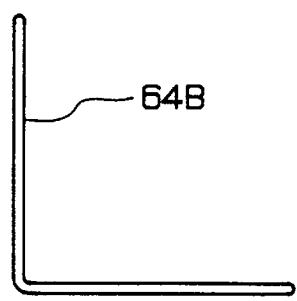
FIG. 9F is an elevational view of one of the plurality of springs of FIG. 9E.
Figure 9G:
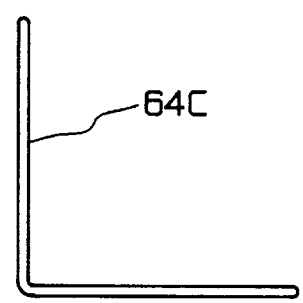
FIG. 9G is an elevational view of another of the plurality of springs of FIG. 9E.
Figure 9H:
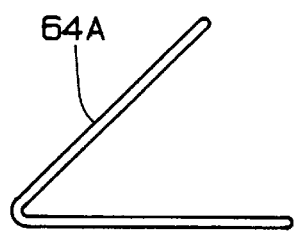
FIG. 9H is an elevational view of yet another of the plurality of springs of FIG. 9E.
Figure 9I:
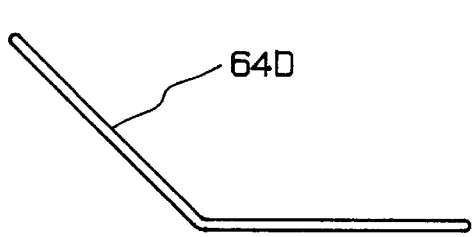
FIG. 9I is an elevational view of still another of the plurality of springs of FIG. 9E.

One type of graft prosthesis which may be used is a graft, generally designated by the reference numeral 60 and shown n FIGS. 9A–9E. Graft 60 includes a body portion 61 having a length slightly larger than the distance between upstream site 21 and downstream site 31. Graft 60 has an outwardly extending flanged end portion 62 as shown in FIGS. 9A, 9C, 9D and 9E. End portion 62 is resiliently maintained outwardly extending by four springs 64A–64D as shown in FIGS. 9B and 9E–9I. In their relaxed state, springs 64A–64D maintain end portion 62 within a plane P1 as shown in FIG. 9A. It should be noted that a number of springs other than four may be used, if desired, to maintain end portion 62 outwardly extending as previously shown and described. Graft 60 further includes a second end portion 63 having a design similar to that of a conventional prosthetic graft as shown in FIG. 9A. Graft 60 is preferably made of synthetic fibers. By way of example, graft 60 can be made from the material sold under the trademark Dacron by E.I. du Pont de Nemours & Co., Inc. of Wilmington, Del. Body portion 61 and end portion 62 are integrally formed together with springs 64A–64D maintained integrally within the end portion 62 and a portion of the sidewalls of body portion 61 as shown in FIGS. 9B and 9E. Graft 60 maintains its shape as shown in FIGS. 9A–9E absent application of external forces thereto and also graft 60 will revert back to such shape upon termination of such external forces thereto.

Figure 10A:
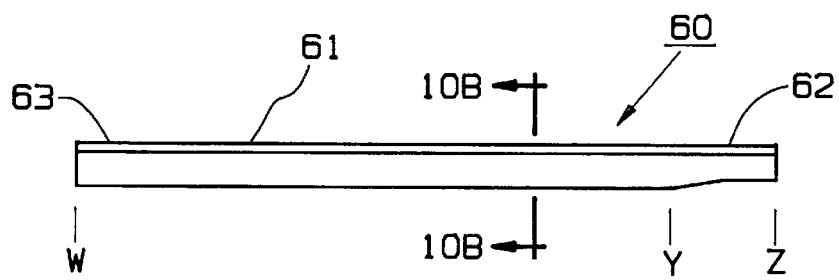
FIG. 10A is an elevational view of the graft prosthesis of FIG. 9A wherein the graft prosthesis is in a rolled configuration.
Figure 10B:
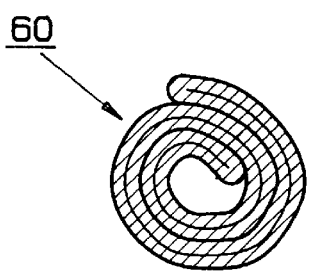
FIG. 10B is a cross-sectional view taken along the line 10B—10B of FIG. 10A as viewed in the direction of the arrows.
Figure 11B:
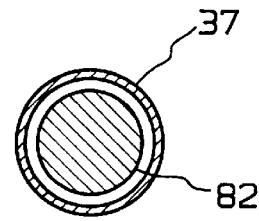
FIG. 11B is a cross-sectional view taken along the line 11B—11B of FIG. 11A as viewed in the direction of the arrows.
Figure 12:
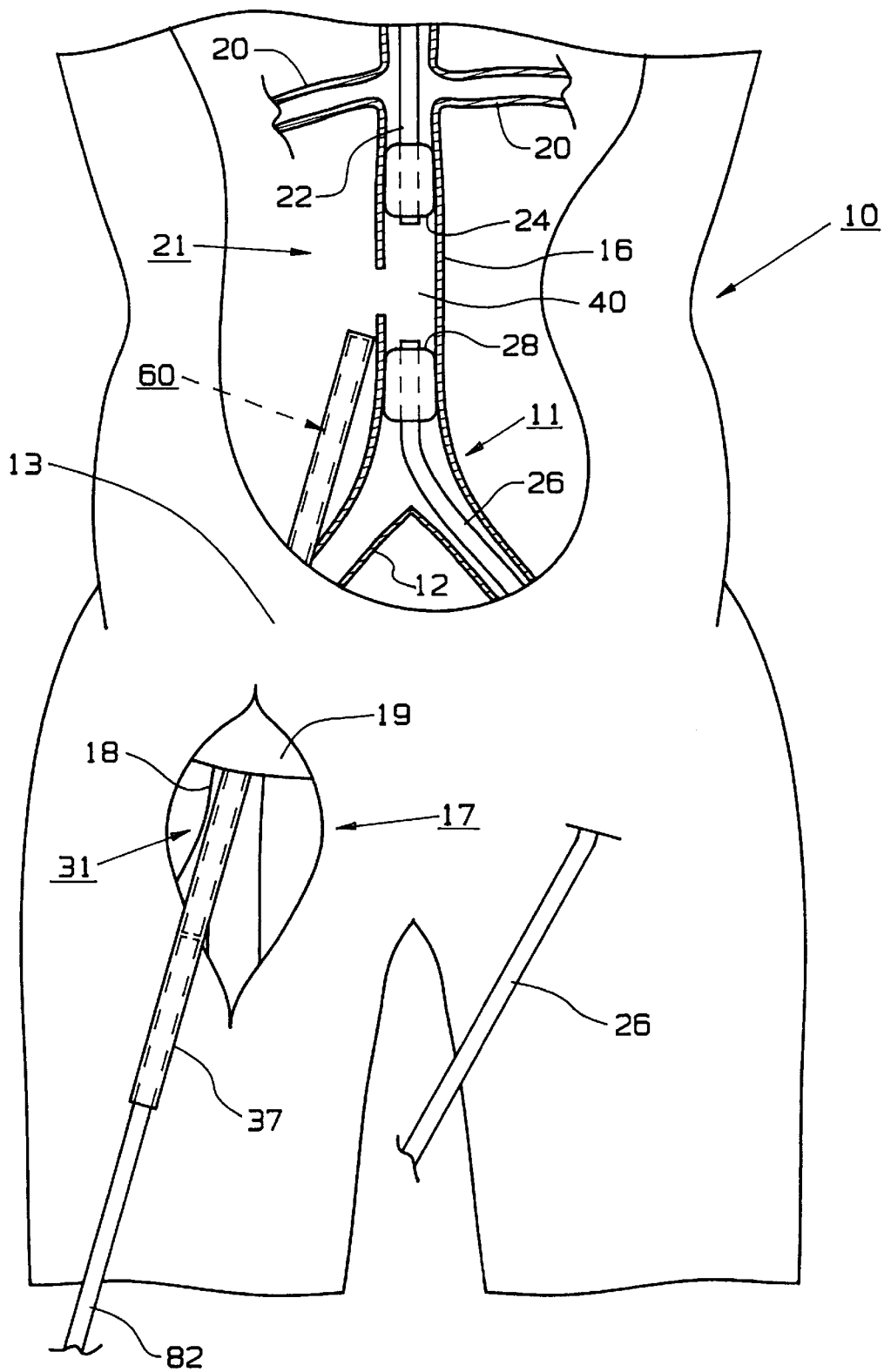
FIG. 12 is a view similar to FIG. 8 but showing the scissors device removed from the laparoscope and replaced with the graft prosthesis and plunger of FIG. 11A in accordance with the preferred method of the present invention.
Figure 13:
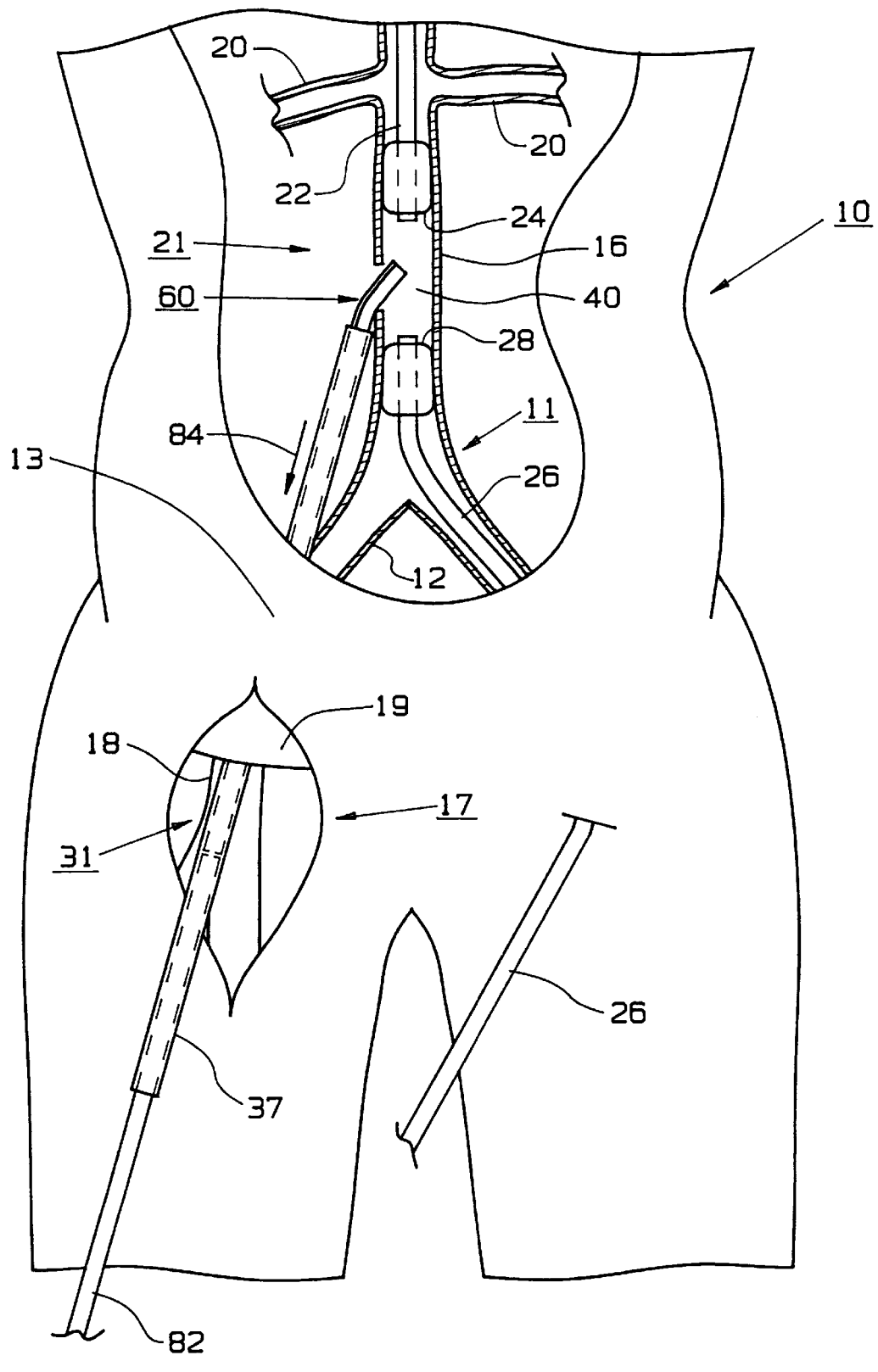
FIG. 13 is a view similar to FIG. 12 but showing the graft prosthesis being advanced out the distal end of the laparoscope in accordance with the preferred method of the present invention.
Figure 14:
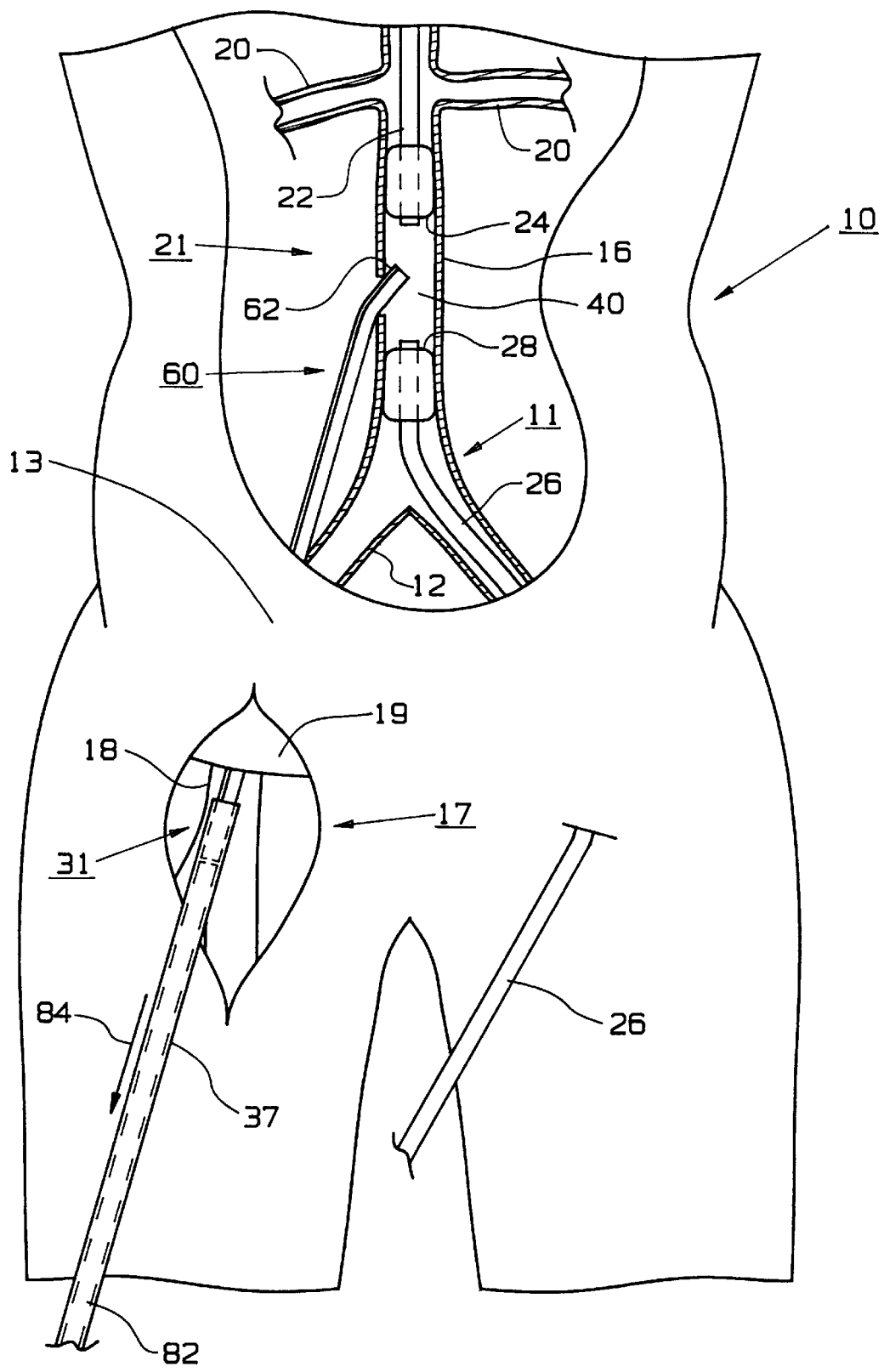
FIG. 14 is a view similar to FIG. 13 but showing the graft prosthesis being further advanced out the distal end of the laparoscope in accordance with the preferred method of the present invention.
Figure 15:
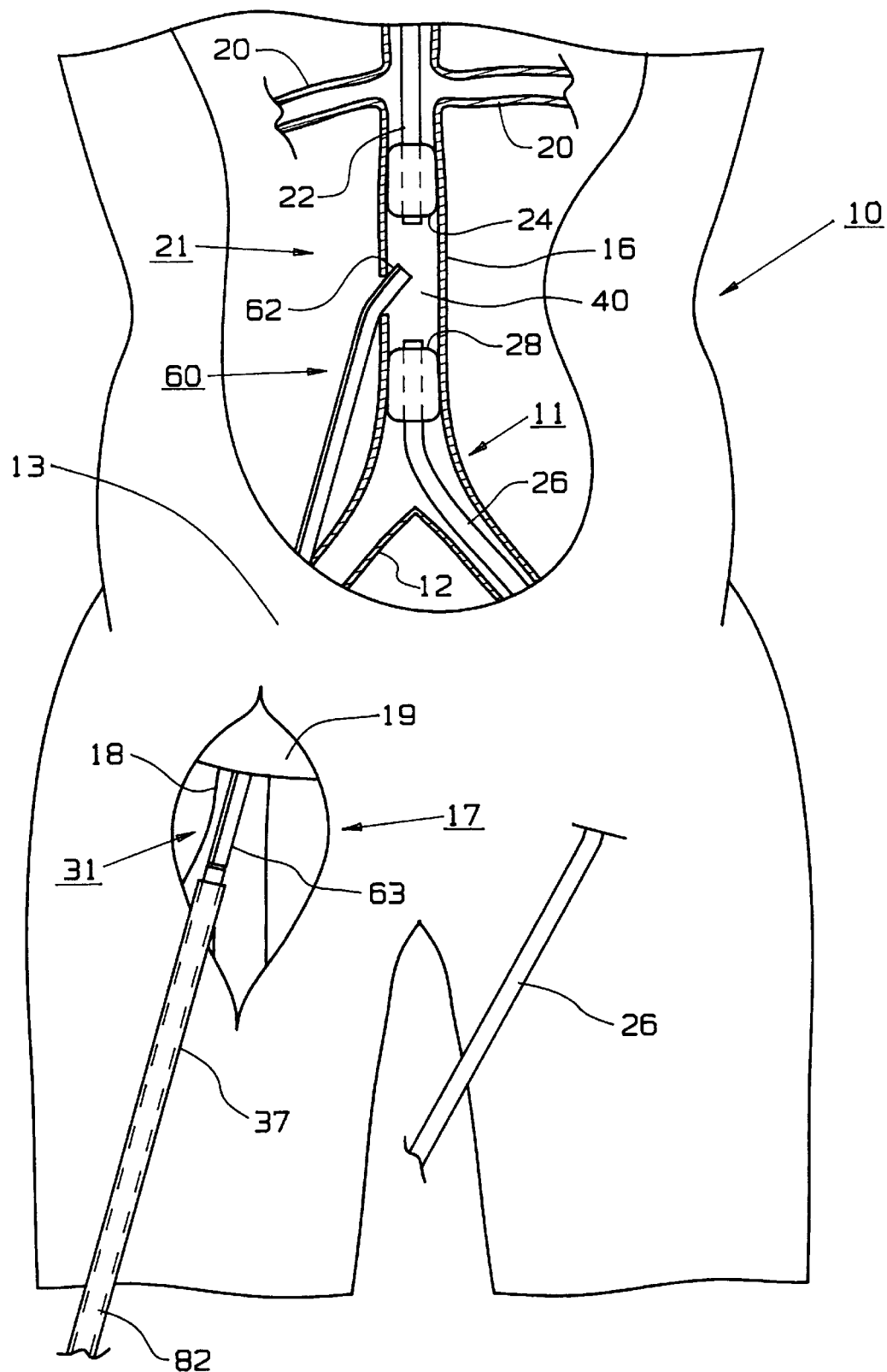
FIG. 15 is a view similar to FIG. 14 but showing the graft prosthesis being yet further advanced out the distal end of the laparoscope in accordance with the preferred method of the present invention.
Figure 16:
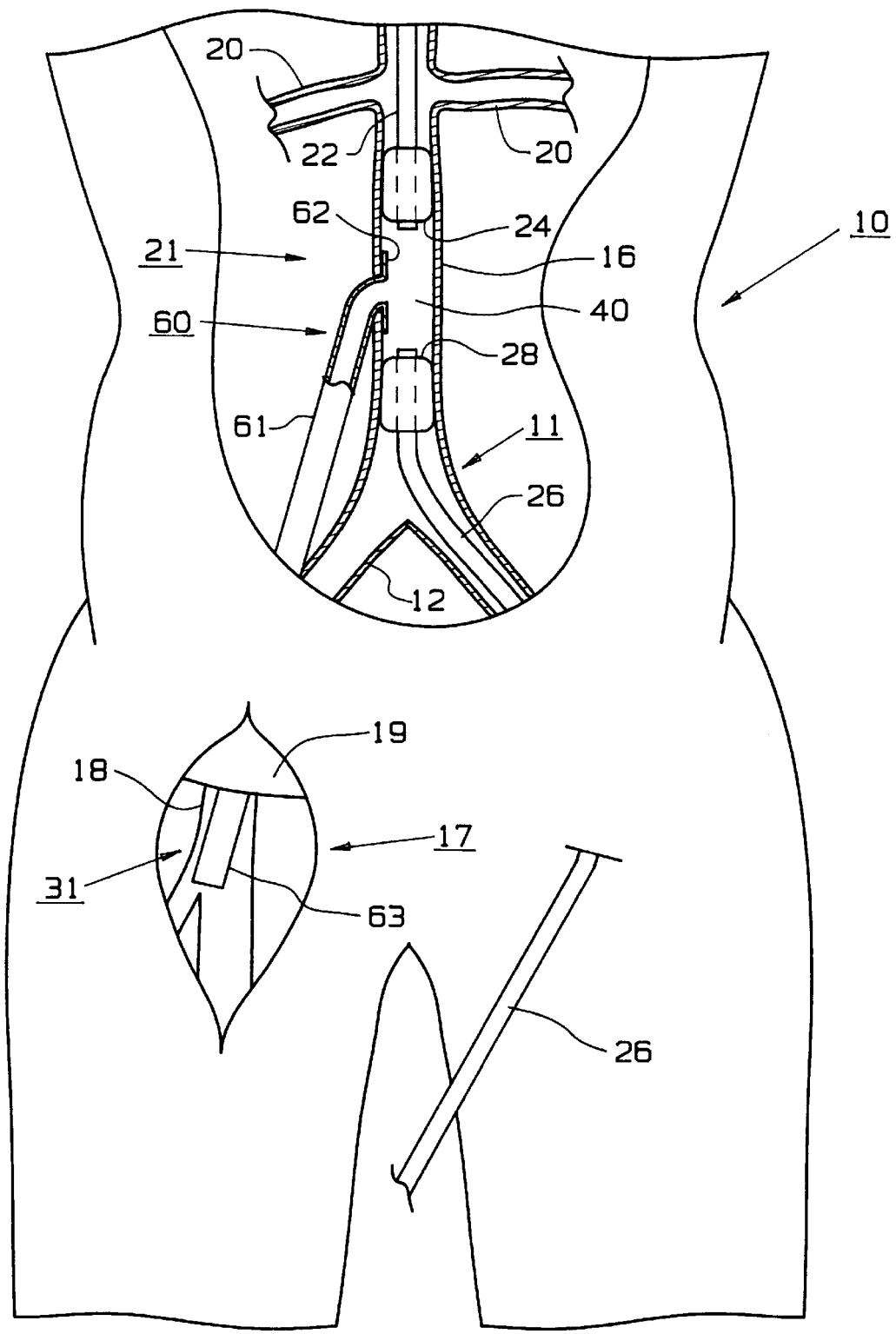
FIG. 16 is a view similar to FIG. 15 but showing the laparoscope removed from the surgical incision and showing the graft prosthesis after it had reverted back to its prerolled configuration in accordance with the preferred method of the present invention.

Graft 60 is positioned within the open central lumen defined in laparoscope 37. In order to achieve the above, graft 60 is preferably rolled into a substantially cylindrical shape as shown in FIGS. 10A and 10B. End portion 62 of graft 60 is manipulated to lie substantially parallel to body portion 61 of graft 60 while graft 60 is in its rolled configuration as shown in FIG. 10A. The outer diameter of graft 60, in its rolled configuration, from point W to point Y is larger than the outer diameter of the rolled graft from point Y to point Z as shown in FIG. 10A. The above is due to the angular construction of end portion 62 as shown in FIG. 9A. The outer diameter of the rolled graft from point W to point Y is slightly smaller than the inner diameter of laparoscope 37. As a result, in its rolled configuration, graft 60 can be positioned within the open central lumen of laparoscope 37. Moreover, graft 60 can be maintained in its rolled configuration while positioned in the central lumen of laparoscope 37 due to the inner diameter thereof. Graft 60 is then inserted into the proximal end of the central lumen of laparoscope 37 and advanced until its full length is entirely therein. A plunger 82 is insertable into the central lumen of laparoscope 37 as shown in FIGS. 11A and 11B. Plunger 82 has a length sufficient to span the length of laparoscope 37. Plunger 82 enables an operator to selectively position graft 60 within body 10. FIGS. 11A and 12 show graft 60 positioned in the distal portion of the central lumen of laparoscope 37 after being advanced by plunger 82. Laparoscope 37 with graft 60 contained therein is then advanced and manipulated such that the distal end of the laparoscope is advanced through the communicating aperture near upstream site 21 and into isolated region 40. While the plunger is held stationary, laparoscope 37 is then withdrawn axially over plunger 82 and graft 60 in the direction of arrow 84 as sequentially shown in FIGS. 13–15. This allows graft 60 in its rolled configuration to be delivered out the distal end of laparoscope 37. FIG. 15 shows end portion 62 of graft 60 positioned within upstream isolated region 40 and end portion 63 of graft 60 positioned at downstream site 31. Since graft 60 is no longer held in its rolled configuration by the inner diameter of the open central lumen of laparoscope 37, graft 60 becomes unrolled and reverts to its prerolled configuration as shown in FIG. 16. Injection of a saline solution into graft 60, via end portion 63, may be performed to facilitate the reverting of graft 60 to its prerolled configuration. Alternatively, an additional laparoscope may be used to manipulate graft 60 to its prerolled configuration. Alternatively, a balloon-tip catheter may be advanced into graft 60 via end portion 63 and the graft converted to its prerolled configuration by inflation and deflation of the balloon along various segments of the graft.

Also shown in FIG. 16, end portion 62 of graft 60 is positioned within upstream isolated region 40 near upstream site 21 and end portion 63 of graft 60 is positioned at downstream site 31 while body portion 61 of graft 60 is positioned outside of blood vessel 11. Note that end portion 62 has also reverted back to its prerolled configuration so that such end portion is outwardly extending relative to body portion 61 of graft 60.

Another step according to the preferred method of the present invention includes forming an anastomosis between end portion 62 of graft 60 and blood vessel 11 near upstream site 21.

Figure 17:
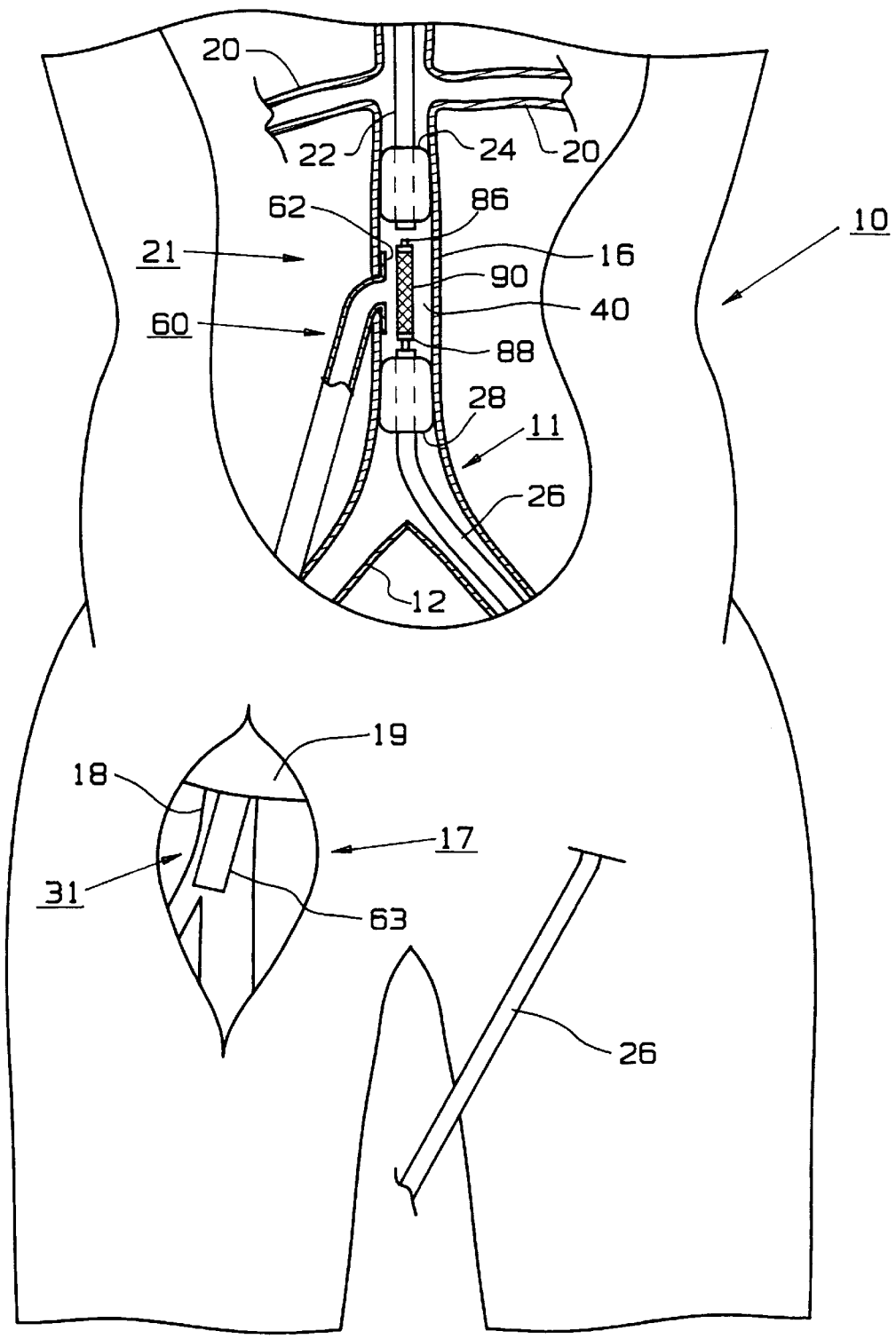
FIG. 17 is a view similar to FIG. 16 but showing a third balloon-tip catheter having a balloon thereon and further having an expandable stent, in its unexpanded state, positioned over the balloon, advanced to a position within the blood vessel in accordance with the preferred method of the present invention.
Figure 18:
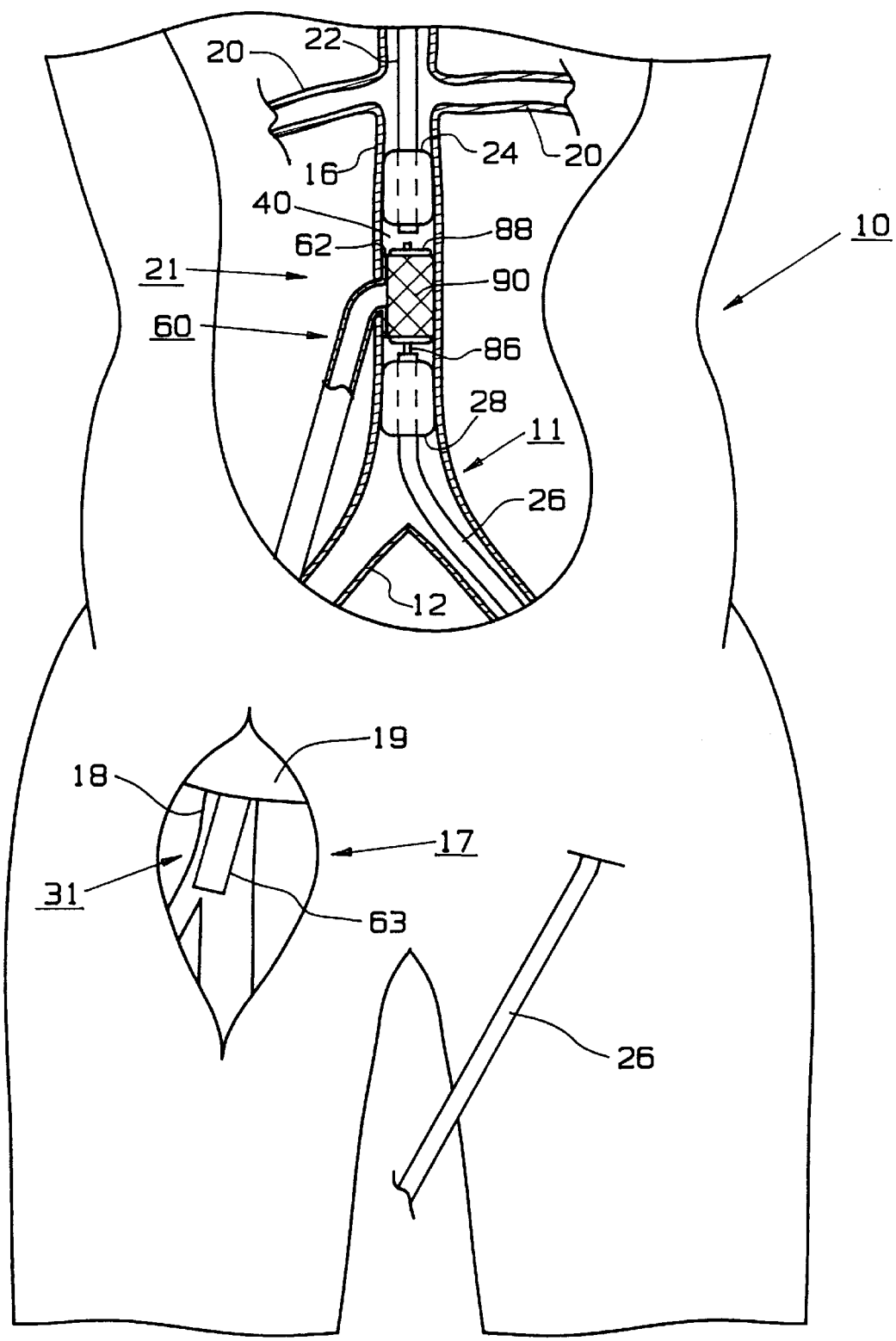
FIG. 18 is a view similar to FIG. 17 but showing the balloon of the third balloon-tip catheter inflated so as to expand the stent in to its expanded configuration in accordance with the preferred method of the present invention.
Figure 19A:
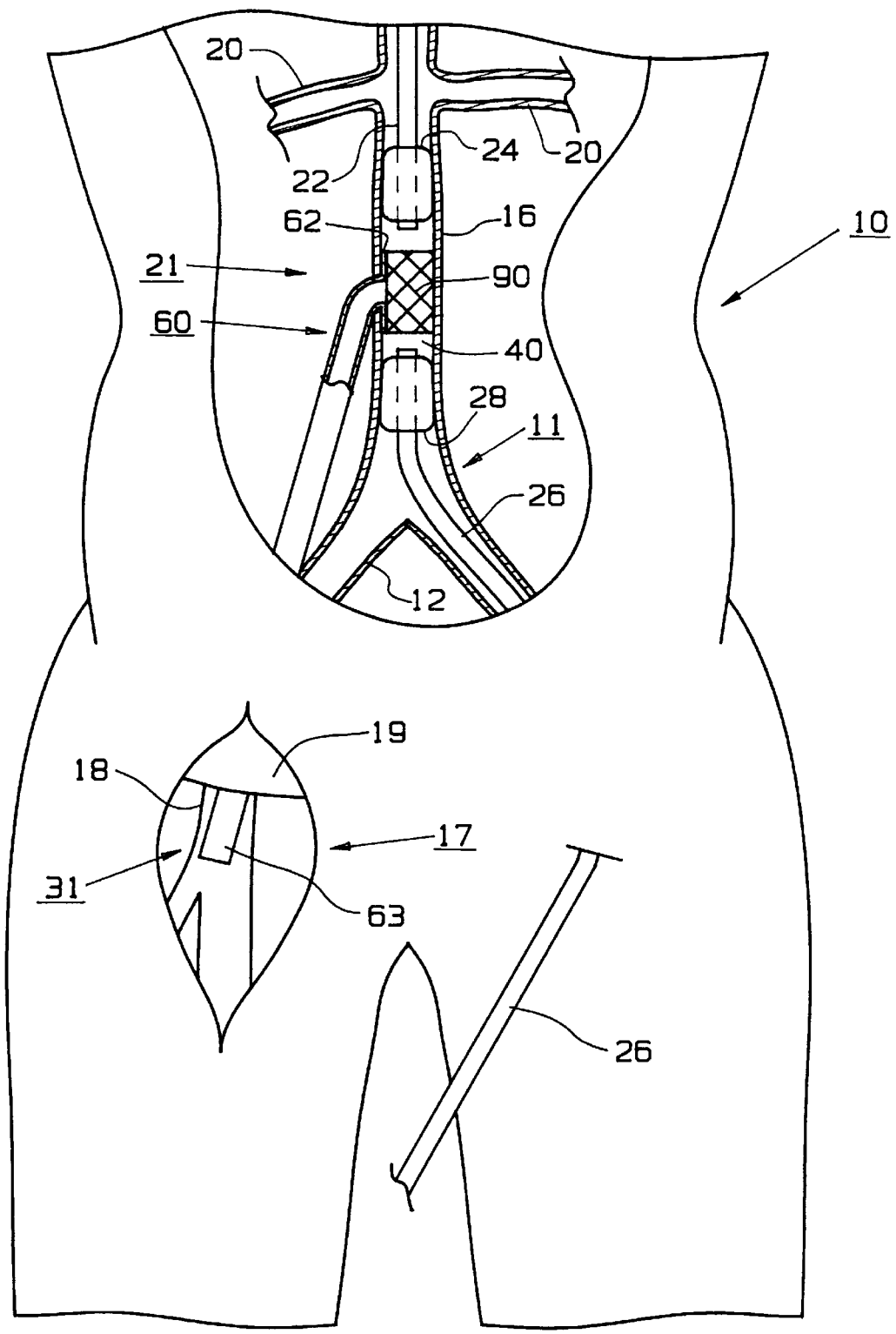
FIG. 19A is a view similar to FIG. 18 but showing the third balloon-tip catheter removed from the blood vessel and showing the stent expanded to form an anastomosis between one end of the graft prosthesis and the blood vessel in accordance with the preferred method of the present invention.

A balloon-tip catheter 86 having a balloon 88 thereon and further having an expandable stent 90, in its unexpanded configuration, positioned over balloon 88 is advanced through the open central lumen of catheter 26 until its distal end is located within upstream isolated region 40 near upstream site 21 (see FIG. 17). Catheter 86 is further advanced until balloon 88 is positioned substantially adjacent end portion 62 of graft 60 as shown in FIG. 17. Balloon 88 is then inflated to expand stent 90 to its expanded configuration such that end portion 62 is secured between stent 90 and the sidewall of blood vessel 11 near upstream site 21 as shown in FIG. 18. Balloon 88 is then deflated and catheter 86 is then removed from body 10 via the central lumen of catheter 26. FIG. 19A shows body 10 after catheter 86 is removed therefrom. Moreover, FIGS. 20A–20C show end portion 62 of graft 60 being forced into the sidewall of blood vessel 11 by stent 90 (in its expanded configuration) such that graft 60 is secured to blood vessel 11 near upstream site 21 at its end portion 62.

One stent which may be used, with a minor degree of modification, in carrying out the preferred method of the present invention is disclosed in U.S. Pat. No. 4,776,337 issued to Palmaz on Oct. 11, 1988, the pertinent part of the disclosure of which is herein incorporated by reference. Such modification would be to provide stent 90 with an outer diameter (in its fully expanded configuration) that is larger than the inner diameter of blood vessel 11 near upstream site 21.

Note that stent 90 includes a plurality of intersecting bars 71 which span the orifice of graft 60 near end portion 62 as shown in FIG. 20B. Intersecting bars 71 which span the above orifice do not substantially hinder blood flow through the graft orifice as demonstrated by the technical article entitled "Intravascular Stents to Prevent Occlusion and Restenosis After Transluminal Angioplasty" which was published in the Mar. 19, 1987 edition of the periodical "The New England Journal of Medicine," the pertinent part of the disclosure of which is herein incorporated by reference.

Further modification may be readily made to stent 90 whereby stent 90 would have an opening defined in its sidewall which is of similar dimensions to the orifice of graft 60 near end portion 62. Such opening would have no intersecting bars traversing thereover. The above modification would allow stent 90 to be positioned within blood vessel 11 near upstream site 21 wherein the above opening would be substantially superimposed over the orifice of graft 60 near end portion 62. This would allow blood to flow through the connection between blood vessel 11 and graft 60 near upstream site 21 in an unimpeded manner.

Figure 19B:
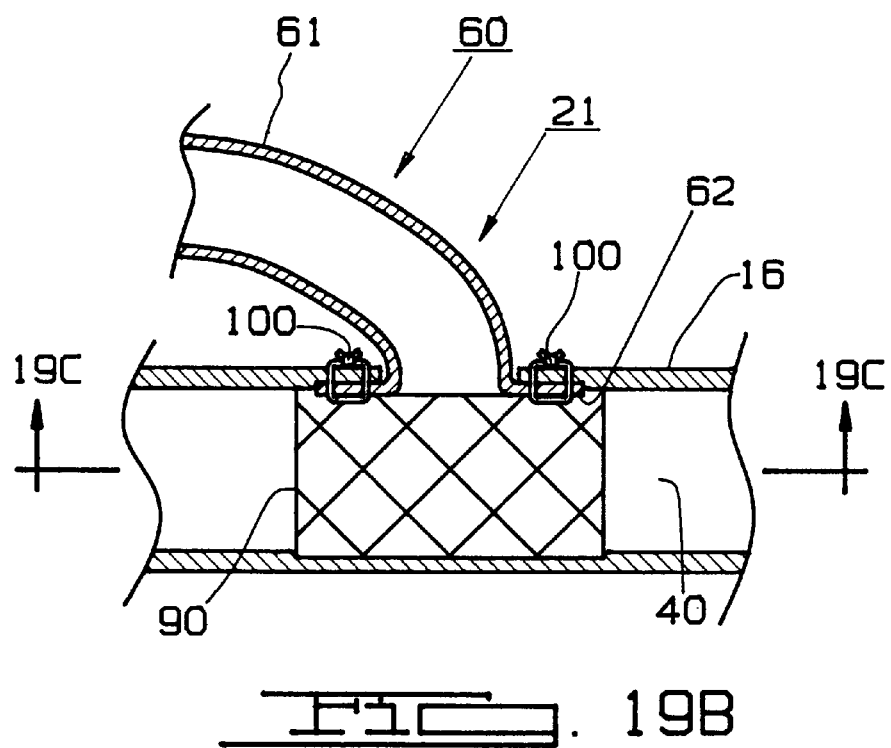
FIG. 19B is an enlarged schematic side elevational view showing a number of sutures tied to the sidewall of the blood vessel so as to secure the end portion of the graft and the stent thereto as a possible additional procedure in order to further ensure the integrity of the anastomosis of FIG. 19A.
Figure 19C:
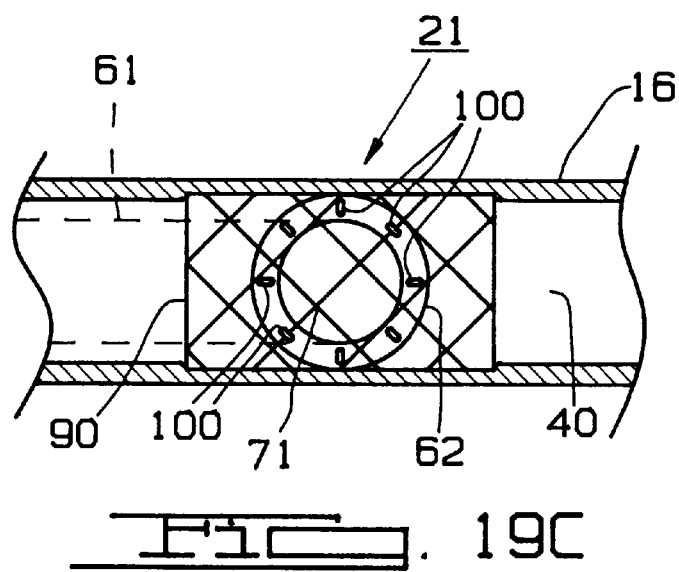
FIG. 19C is a cross-sectional view taken along the line 19C—19C of FIG. 19B as viewed in the direction of the arrows.
Figure 19D:
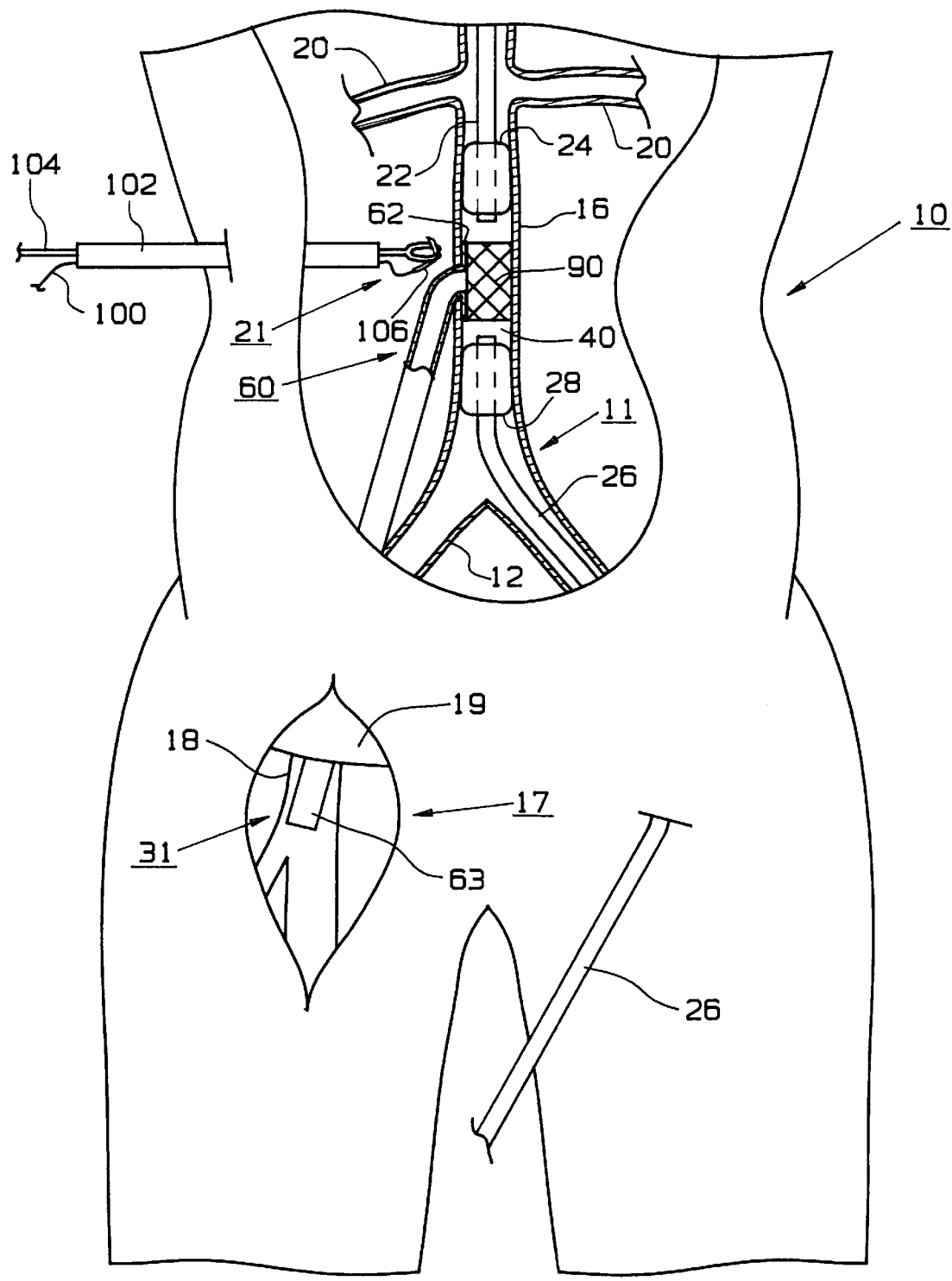
FIG. 19D is a view similar to FIG. 19A but showing a laparoscope (depicted schematically) inserted through an incision in the epidermis of the body and into the peritoneal cavity, and further showing a grasper holding a curved needle with an end of a suture attached thereto wherein the distal end of the grasper is positioned at the upstream site.

As a possible additional procedure in order to further ensure the integrity of the anastomosis between end portion 62 of graft 60 and blood vessel 11 near upstream site 21, a number of sutures 100 may be tied to the sidewall of blood vessel 11 so as to further secure end portion 62 and stent 90 to the sidewall of blood vessel 11 as schematically shown in FIGS. 19B and 19C. This is accomplished by inserting a laparoscope 102 (which is similar to laparoscope 37) having an open central lumen into human body 10 until its distal end is near upstream site 21. Thereafter, a grasper 104 is advanced through the central lumen of laparoscope 102. The grasper 104 has in its grasp a curved needle 106 having an end of suture 100 attached thereto as shown in FIG. 19D. By manipulating the distal end of grasper 104, the needle 106 and the end of suture 100 are passed through the sidewall of blood vessel 11 and end portion 62 of graft 60 and into blood vessel 11. With continued manipulation, the needle 106 and the end of suture 100 are then brought back out of blood vessel 11. The suture 100 is then tied by standard laparoscopic techniques. One article that refers to standard laparoscopic techniques for tying sutures is entitled "Laparoscopic Choledocholithotomy", which was published in Volume 1, Number , 1991 edition of the "Journal of Laparoendoscopic Surgery" (Mary Ann Liebert, Inc., Publishers), pages 79–82, and another article that refers to standard laparoscopic techniques for tying sutures is entitled "Improvement in Endoscopic Hernioplasty: Transcutaneous Aquadissection of the Musculofascial Defect and Preperitoneal Endoscopic Patch Repair", which was published in Volume 1, Number 2, 1991 edition of the "Journal of Laparoendoscopic Surgery" (Mary Ann Liebert, Inc., Publishers), pages 83–90, the pertinent part of both of the above articles of which is herein incorporated by reference. A number of other sutures 100 are then tied to the sidewall of blood vessel 11 and end portion 62 of graft 60 in a manner similar to that hereinbefore described so as to further secure end portion 62 to the sidewall of blood vessel 11 as schematically shown in FIGS. 19B and 19C. One or more additional laparoscopes and associated laparoscopic operating instruments may be employed using standard laparoscopic techniques to assist in the above suturing procedure. Of course, sutures 100 may be sewn in a conventional running fashion so as to secure end portion 62 to the sidewall of blood vessel 11. Also, end portion 62 may be sutured to the sidewall of blood vessel 11 prior to the placement of stent 90 within blood vessel 11.

Figure 19E:
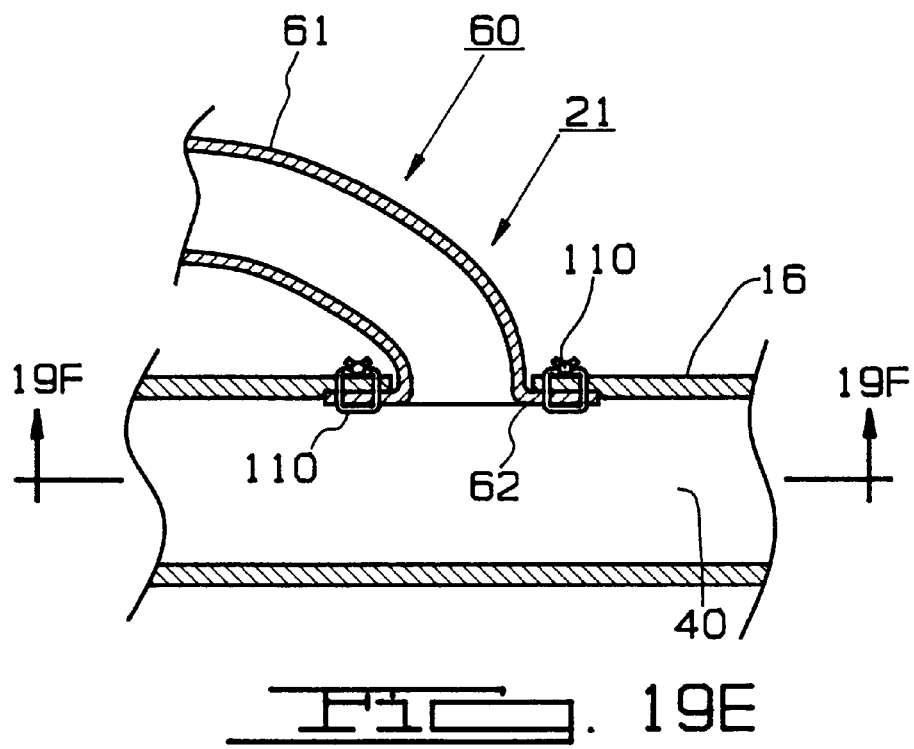
FIG. 19E is an enlarged schematic side elevational view showing a number of sutures tied to the sidewall of the blood vessel so as to secure the end portion of the graft thereto (without the use of the stent), wherein the end portion of the graft is positioned within the upstream isolated region, as an alternative procedure in forming an anastomosis between the end portion of the graft and the blood vessel.
Figure 19F:
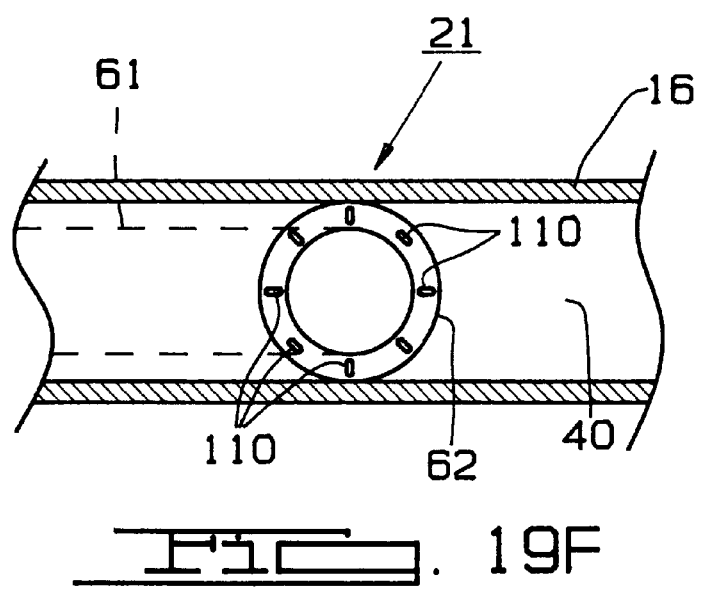
FIG. 19F is a cross-sectional view taken along the line 19F—19F of FIG. 19E as viewed in the direction of the arrows.

Alternatively, the step of forming an anastomosis between end portion 62 of graft 60 and blood vessel 11 near upstream site 21 may be accomplished by suturing alone (i.e. without the use of stent 90). In particular, once end portion 62 of graft 60 is positioned within upstream isolated region 40 near upstream site 21 as shown in FIG. 16, end portion 62 is sutured to the sidewall of blood vessel 11 as schematically shown in FIGS. 19E and 19F. Note that in this alternative step, end portion 62 is sutured to an interior portion of blood vessel 11 as schematically shown in FIGS. 19E and 19F. Also note that end portion 62 is sutured to the sidewall of blood vessel 11 so as to be positioned substantially adjacent a portion of the sidewall of blood vessel 11 which substantially surrounds the arteriotomy. This is accomplished by tying a number of sutures 110 to the sidewall of blood vessel 11 and end portion 62 of graft 60 so as to secure end portion 62 to the sidewall of blood vessel 11 as schematically shown in FIGS. 19E and 19F. The sutures 110 shown in FIGS. 19E and 19F are applied in the same manner as the sutures 100 shown in FIGS. 19B, 19C and 19D were applied as described above. Of course, sutures 110 may be sewn in a conventional running fashion so as to secure end portion 62 to the sidewall of blood vessel 11.

Figure 19G:
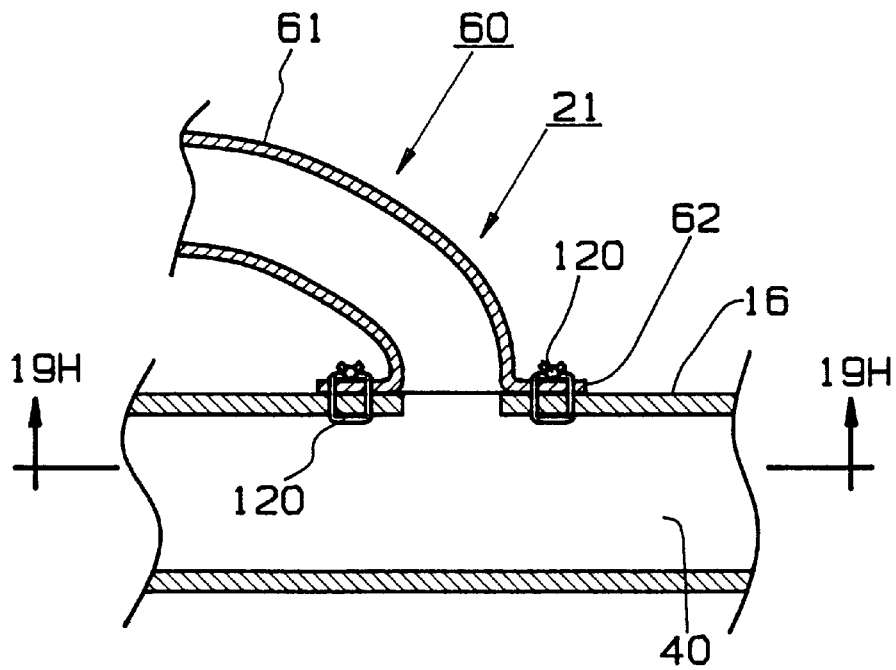
FIG. 19G is an enlarged schematic side elevational view showing a number of sutures tied to the sidewall of the blood vessel so as to secure the end portion of the graft thereto (without the use of the stent), wherein the end portion of the graft is positioned outside of the upstream isolated region, as another alternative procedure in forming an anastomosis between the end portion of the graft and the blood vessel.
Figure 19H:
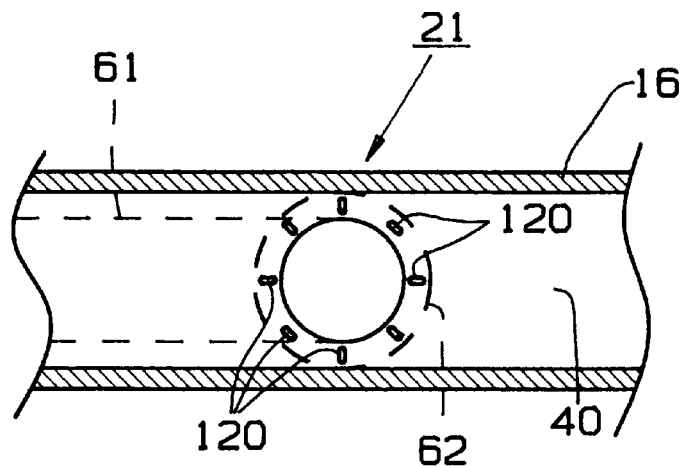
FIG. 19H is a cross-sectional view taken along the line 19H—19H of FIG. 19G as viewed in the direction of the arrows.

As a further alternative, the end portion 62 of graft 60 need not be positioned in upstream isolated region 40 but rather end portion 62 may be positioned adjacent the sidewall of blood vessel 11 so that the communicating aperture (i.e. the arteriotomy) in the sidewall of blood vessel 11 near upstream site 21 is aligned with the central passage of graft 60. At this position, end portion 62 is sutured to the sidewall of blood vessel as schematically shown in FIGS. 19G and 19H. Note that in this further alternative step, end portion 62 is sutured to an exterior portion of blood vessel 11 as schematically shown in FIGS. 19G and 19H. Also note that end portion 62 is sutured to the sidewall of blood vessel 11 so as to be positioned substantially adjacent a portion of the sidewall of blood vessel 11 which substantially surrounds the arteriotomy. This is accomplished by tying a number of sutures 120 to the sidewall of blood vessel 11 and end portion 62 of graft 60 so as to secure end portion 62 to the sidewall of blood vessel 11 as schematically shown in FIGS. 19G and 19H. The sutures 120 shown in FIGS. 19G and 19H are applied in the same manner as the sutures 100 shown in FIGS. 19B, 19C and 19D were applied as described above. Of course, sutures 120 may be sewn in a conventional running fashion so as to secure end portion 62 to the sidewall of blood vessel 11.

Figure 21:
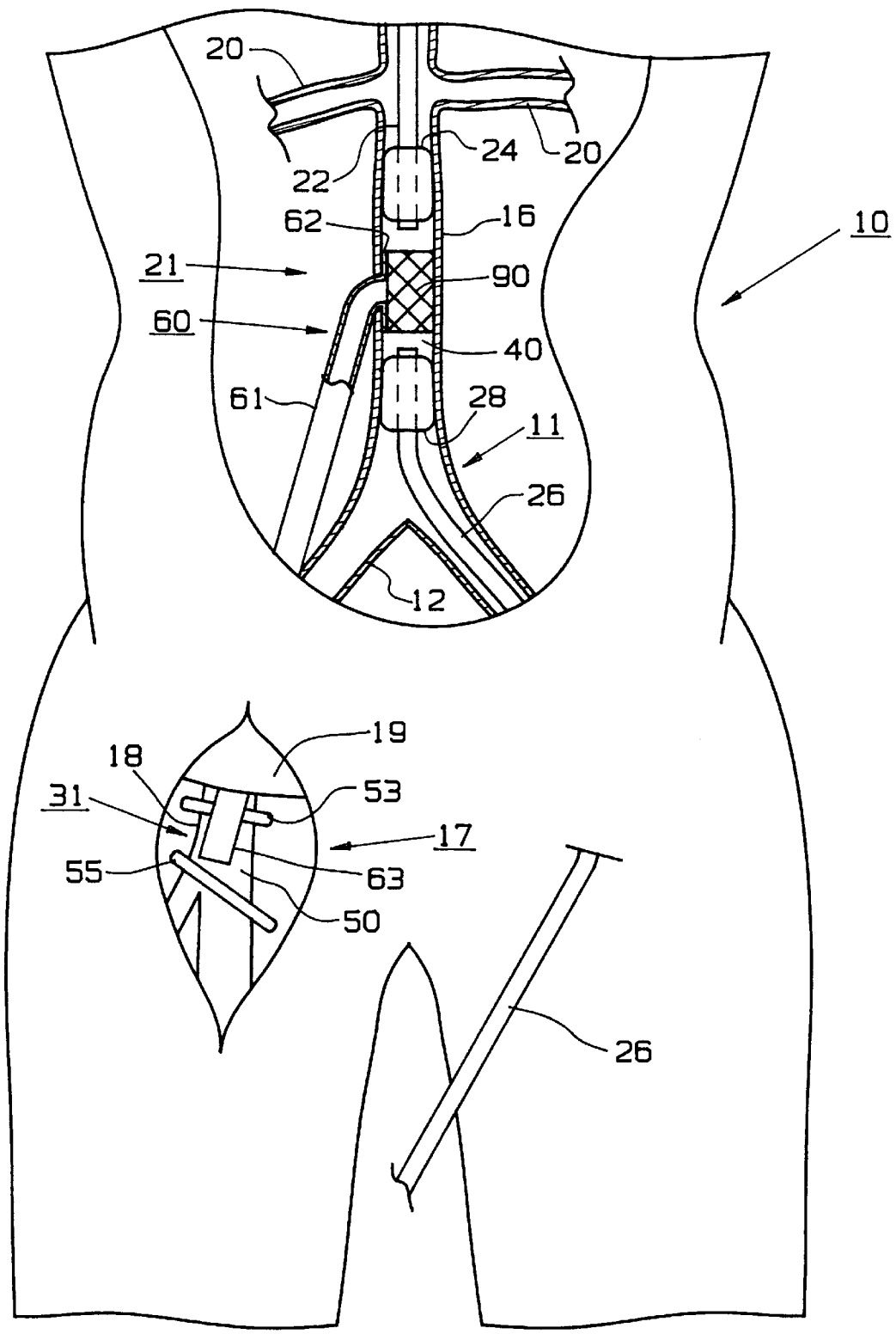
FIG. 21 is a view similar to FIG. 19A but showing a pair of clamps positioned on the blood vessel in accordance with the preferred method of the present invention.

The remainder of the preferred method of the present invention is performed using standard surgical techniques. A book which discloses various standard surgical techniques is entitled "Color Atlas of Vascular Surgery," authored by John S. P. Lumley, published by Wolfe Medical Publications Ltd. of Baltimore, M.d. (1986), printed by W. S. Cowell, Ltd. of Ipswich, United Kingdom, and the pertinent part of the disclosure of which is herein incorporated by reference. More specifically, another step according to the preferred method of the present invention comprises isolating a region 50 of the area within blood vessel 11, located near site 31 downstream of occluded segment 14, from fluid communication with the rest of the area within the blood vessel. Referring now to FIG. 21, a pair of surgical clamps 53 and 55 are positioned on blood vessel 11, one being placed upstream of isolated region 50 and the other being placed downstream of isolated region 50.

Figure 22:
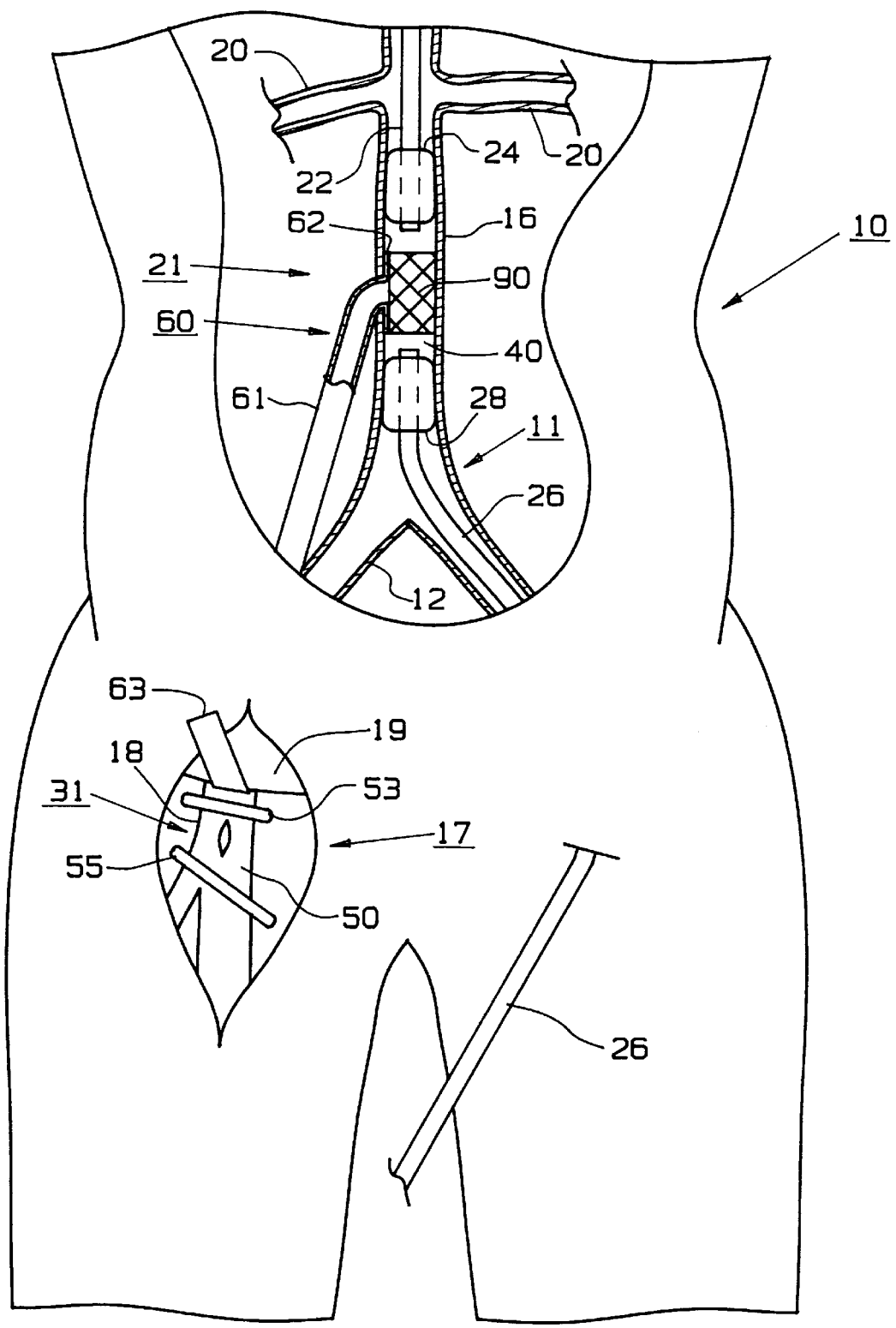
FIG. 22 is a view similar to FIG. 21 but showing an arteriotomy formed in the sidewall of the blood vessel in accordance with the preferred method of the present invention.

Another step according to the method of the present invention comprises making an arteriotomy in the sidewall of blood vessel 11, near downstream site 31, to create a communicating aperture between downstream isolated region 50 and the outside of the blood vessel 11. End portion 63 of graft 60 is retracted by surgical forceps (not shown) to expose blood vessel 11 near downstream site 31 (see FIG. 22). A scalpel puncture is then made in blood vessel 11 near downstream site 31 and thereafter the puncture is extended to the appropriate length with a pair of surgical scissors. FIG. 22 shows the communicating aperture defined in the sidewall of blood vessel 11, near downstream site 31.

Figure 23:
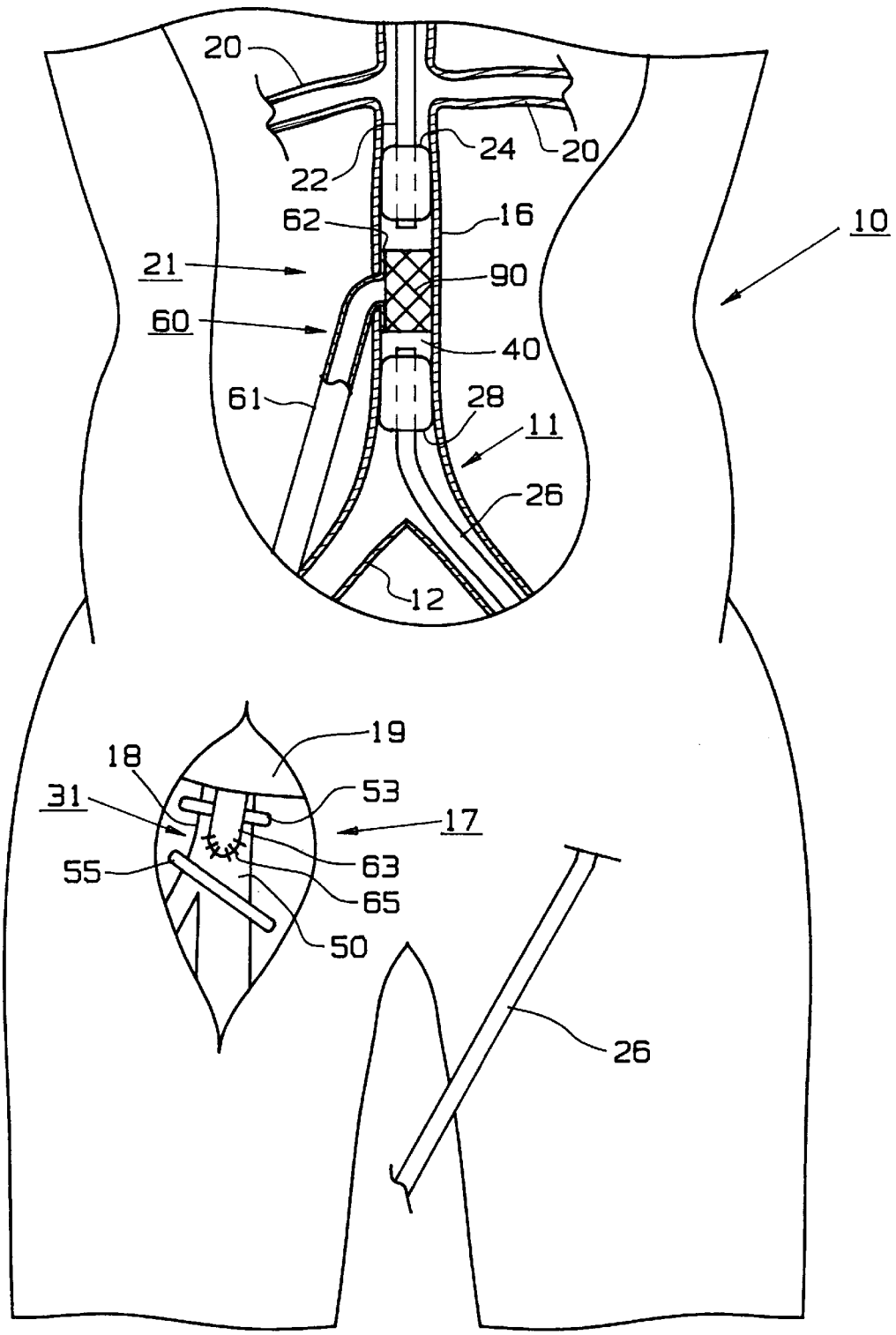
FIG. 23 is a view similar to FIG. 22 but showing an anastomosis formed between the other end the graft prosthesis and the blood vessel in accordance with the preferred method of the present invention.

Another step according to the preferred method of the present invention comprises forming an anastomosis between end portion 63 of graft 60 and blood vessel 11 near downstream site 31. Graft 60 is then cut to an appropriate length and thereafter end portion 63 is cut an appropriate shape for attachment to blood vessel 11. End portion 63 of graft 60 is then surgically stitched with suture 65 to blood vessel 11 near downstream site 31 as shown in FIG. 23.

Figure 24:
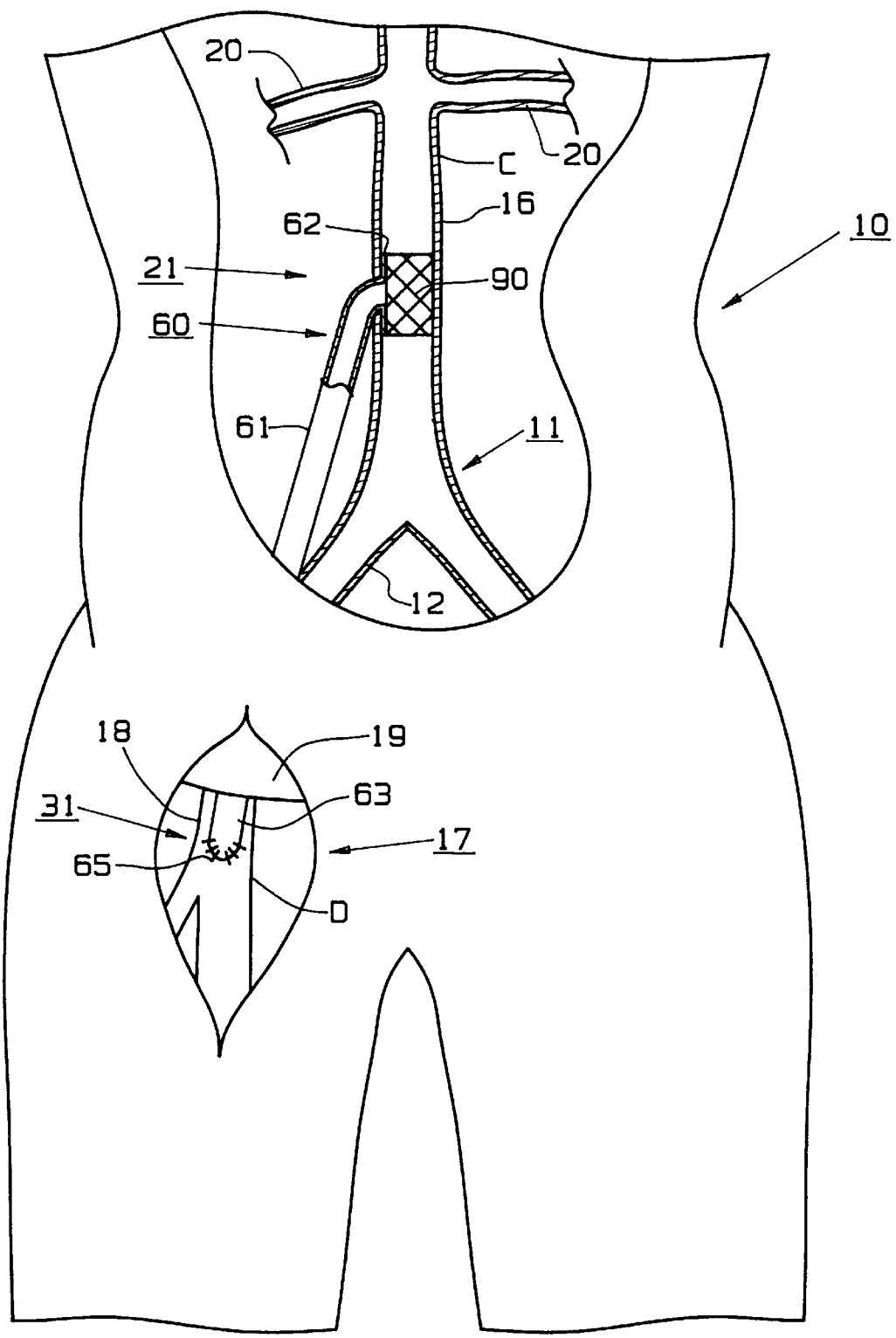
FIG. 24 is a view similar to FIG. 23 but showing the first balloon-tip catheter and the second balloon-tip catheter removed from the blood vessel in accordance with the preferred method of the present invention.

Clamps 53 and 55 are then removed from blood vessel 11, and moreover, balloons 24 and 28 are then deflated and thereafter catheters 22 and 26 are removed from body 10 as shown in FIG. 24. This allows blood to flow to former upstream isolated region 40. Once blood flow reaches former upstream isolated region 40, a flow of blood will enter graft 60 and flow therethrough to former downstream isolated region 50 thereby bypassing occluded segment 14. Consequently, proper blood flow will now exist in body 10 from point C within aorta 16 to point D within right common femoral artery 18 as a result of performing the above described method of bypass of occluded segment 14.

While the invention has been described in detail in the drawings and foregoing description, the same is to be considered as illustrative and not restrictive in character, it being understood that only the preferred embodiments and methods have been shown and described and that all changes and modifications that come within the spirit of the invention are desired to be protected.

For instance, it is possible that left common femoral artery 30 and left inguinal ligament 29 could be exposed via a surgical incision similar to that of incision 17 as hereinbefore described. Thereafter, a Y-shaped graft could be utilized instead of graft 60 as hereinbefore disclosed. The Y-shaped graft could be advanced in a rolled configuration through laparoscope 37 and delivered to a position substantially adjacent blood vessel 11 similar in manner to that hereinbefore described. An additional laparoscope could be inserted into human body 10 through the opening defined between left common femoral artery 30 and left inguinal ligament 29 in a manner substantially similar to that hereinbefore described with respect to the insertion of laparoscope 37 into human body 10. The additional laparoscope could be advanced toward the left limb of the Y-shaped graft and thereafter used to grasp such limb and pull it toward left common femoral artery 30 and subsequently out of the surgical incision near the left common femoral artery. The end portion of the left limb of the Y-shaped graft could be cut to an appropriate length and shape, and thereafter, an anastomosis could be made between such end portion and left common femoral artery 30 similar in manner to that hereinbefore described with regard to right common femoral artery 18 and end portion 63 of graft 60.

Moreover, for example, it is possible that a graft may be utilized which would be similar to graft 60 hereinbefore described, however, both end portions of such graft could be similar in structure to end portion 62 of graft 60. In other words, each graft end could possess an end portion that is resiliently maintained outwardly extending relative to the body portion of the graft. A catheter could be placed into blood vessel 11 at right femoral artery 18 and advanced toward occluded segment 14. Prior to arriving at occluded segment 14, the distal end of the catheter could be manipulated and guided out of blood vessel 11 through a puncture site laparoscopically created in the blood vessel in a manner similar to that hereinbefore described. The catheter could then be advanced substantially adjacent blood vessel 11 over and past occluded segment 14. One or more additional laparoscopes could assist in the above advancement. The distal end of the catheter could then be manipulated and guided to reenter blood vessel 11 at a site upstream of occluded segment 14 through a puncture site laparoscopically created in blood vessel 11 in a manner similar to that hereinbefore described. The graft having a resiliently outwardly extending end portion at each end thereof could then be advanced in rolled configuration through the catheter and delivered to a position substantially adjacent blood vessel 11 similar in manner to that hereinbefore described with respect to graft 60 and laparoscope 37. The graft could have a predetermined length equal to a length slightly larger than the distance between the puncture site located upstream of occluded segment 14 and the puncture site located downstream of occluded segment 14. As a result, the distal end portion of the graft could be positioned within blood vessel 11 at a location upstream of occluded segment 14 and the proximal end portion of the graft could be positioned within blood vessel 11 at a location downstream of occluded segment 14 while the body portion of the graft could be positioned substantially adjacent and outside of blood vessel 11. Of course, an area within the blood vessel near each end portion of the graft could be isolated from fluid communication with the rest of the area within the blood vessel in a manner substantially similar to that hereinbefore described with respect to upstream isolated region 40. After being advanced out the distal end of the catheter, the graft (including each outwardly extending end portion) could revert back to its prerolled configuration as hereinbefore described with respect to graft 60. Thereafter, a stent could be placed, in an expanded configuration, adjacent each of the end portions of the graft within blood vessel 11 in order to secure such end portions of the graft to blood vessel 11 as hereinbefore described with respect to stent 90 and end portion 62 of graft 60.

What I claim is:

1. A method of securing an end portion of a graft to a blood vessel of a patient's circulatory system during a bypass grafting procedure, comprising the steps of:

inhibiting blood flow to a region of the circulatory system by inflating a plurality of balloons within the circulatory system, wherein a segment of the blood vessel is located in the region;

anastomosing the end portion of the graft to the segment of the blood vessel during the blood flow inhibiting step; and creating an arteriotomy in a sidewall of the segment of the blood vessel while (i) all of the plurality of balloons are inflated within the circulatory system, and (ii) prior to the anastomosing step.

2. The method of claim 1, wherein the anastomosing step and the arteriotomy creating step are each performed while the segment of the blood vessel is covered by a substantially intact portion of the epidermis of the body.

3. A method of securing an end portion of a graft to a blood vessel of a patient's circulatory system during a bypass grafting procedure, comprising the steps of:

inhibiting blood flow to a region of the circulatory system by inflating a plurality of balloons within the circulatory system, wherein a segment of the blood vessel is located in the region; and anastomosing the end portion of the graft to the segment of the blood vessel during the blood flow inhibiting step, wherein the blood vessel is an aorta, wherein the blood flow inhibiting step includes the step of inflating a first balloon of the plurality of balloons within the aorta to occlude blood flow at a first location in the aorta, wherein the blood flow inhibiting step further includes the step of inflating a second balloon of the plurality of balloons within the aorta to occlude blood flow at a second location in the aorta, wherein the first location is spaced apart from the second location, and further comprising the step creating an arteriotomy in a sidewall of the segment of the aorta between the first location and the second location while (i) all of the plurality of balloons are inflated within the circulatory system, and (ii) prior to the anastomosing step.

4. A method of securing an end portion of a graft to a blood vessel of a patient's circulatory system during a bypass grafting procedure, comprising the steps of:

inhibiting blood flow to a region of the circulatory system by inflating a plurality of balloons within the circulatory system, wherein a segment of the blood vessel is located in the region; and anastomosing the end portion of the graft to the segment of the blood vessel during the blood flow inhibiting step, wherein the blood flow inhibiting step includes the step of inflating a first balloon of the plurality of balloons within the blood vessel to occlude blood flow at a first location in the blood vessel, wherein the blood flow inhibiting step further includes the step of inflating a second balloon of the plurality of balloons within the blood vessel to occlude blood flow at a second location in the blood vessel, wherein the first location is spaced apart from the second location, and further comprising the step of creating an arteriotomy in a sidewall of the segment of the blood vessel between the first location and the second location while (i) all of the plurality of balloons are inflated within the circulatory system, and (ii) prior to the anastomosing step.

5. A method of securing an end portion of a graft to a blood vessel of a patient's circulatory system during a bypass grafting procedure, comprising the steps of:

inhibiting blood flow to a region of the circulatory system by inflating a plurality of balloons within the circulatory system, wherein a segment of the blood vessel is located in the region; and anastomosing the end portion of the graft to the segment of the blood vessel during the blood flow inhibiting step, wherein (i) a first balloon of the plurality of balloons is included on a first distal portion of a first catheter, and (ii) a second balloon of the plurality of balloons is included on a second distal portion of a second catheter, and further comprising the step of:

advancing the first catheter and the second catheter within the circulatory system so as to position the first balloon and the second balloon within the circulatory system prior to the blood flow inhibiting step.

6. A method of securing an end portion of a graft to a blood vessel of a patient's circulatory system during a bypass grafting procedure, comprising the steps of:

inflating a plurality of balloons within the circulatory system to prevent blood flow through a region of the circulatory system which includes a segment of the blood vessel;

anastomosing the end portion of the graft to the segment of the blood vessel while the plurality of balloons are inflated within the circulatory system; and creating an arteriotomy in a sidewall of the segment of the blood vessel while (i) all of the plurality of balloons are inflated within the circulatory system, and (ii) prior to the anastomosing step.

7. The method of claim 6, wherein the anastomosing step and the arteriotomy creating step are each performed while the segment of the blood vessel is covered by a substantially intact portion of the epidermis of the body.

8. A method of securing an end portion of a graft to a blood vessel of a patient's circulatory system during a bypass grafting procedure, comprising the steps of:

inflating a plurality of balloons within the circulatory system to prevent blood flow through a region of the circulatory system which includes a segment of the blood vessel; and anastomosing the end portion of the graft to the segment of the blood vessel while the plurality of balloons are inflated within the circulatory system wherein the blood vessel is an aorta, wherein the inflating step includes the step of inflating a first balloon of the plurality of balloons within the aorta to occlude blood flow at a first location in the aorta, wherein the inflating step further includes the step of inflating a second balloon of the plurality of balloons within the aorta to occlude blood flow at a second location in the aorta, wherein the first location is spaced apart from the second location, and further comprising the step of creating an arteriotomy in a sidewall of the segment of the aorta between the first location and the second location while (i) all of the plurality of balloons are inflated within the circulatory system, and (ii) prior to the anastomosing step.

9. A method of securing an end portion of a graft to a blood vessel of a patient's circulatory system during a bypass grafting procedure, comprising the steps of:

inflating a plurality of balloons within the circulatory system to prevent blood flow through a region of the circulatory system which includes a segment of the blood vessel; and anastomosing the end portion of the graft to the segment of the blood vessel while the plurality of balloons are inflated within the circulatory system, wherein the inflating step includes the step of inflating a first balloon of the plurality of balloons within the blood vessel to occlude blood flow at a first location in the blood vessel, wherein the inflating step further includes the step of inflating a second balloon of the plurality of balloons within the blood vessel to occlude blood flow at a second location in the blood vessel, wherein the first location is spaced apart from the second location, and further comprising the step of creating an arteriotomy in a sidewall of the segment of the blood vessel between the first location and the second location while (i) all of the plurality of balloons are inflated within the circulatory system, and (ii) prior to the anastomosing step.

10. A method of securing an end portion of a graft to a blood vessel of a patient's circulatory system during a bypass grafting procedure, comprising the steps of:

inflating a plurality of balloons within the circulatory system to prevent blood flow through a region of the circulatory system which includes a segment of the blood vessel; and anastomosing the end portion of the graft to the segment of the blood vessel while the plurality of balloons are inflated within the circulatory system, wherein (i) a first balloon of the plurality of balloons is included on a first distal portion of a first catheter, and (ii) a second balloon of the plurality of balloons is included on a second distal portion of a second catheter, and further comprising the step of:

advancing the first catheter and the second catheter within the circulatory system so as to position the first balloon and the second balloon within the circulatory system prior to the inflating step.

11. A method of implanting an end portion of a graft within a patient's body during a bypass grafting procedure, with the body including a circulatory system, comprising the steps of:

isolating a region of the area within the circulatory system from fluid communication with the rest of the area within the circulatory system to inhibit blood flow through a segment of a blood vessel located within the region, wherein the isolating step includes the step of inflating a plurality of balloons within the circulatory system to occlude blood flow within the circulatory system; and anastomosing the end portion of the graft to the segment of the blood vessel during the isolating step; and creating an arteriotomy in a sidewall of the segment of the blood vessel while (i) all of the plurality of balloons are inflated within the circulatory system, and (ii) prior to the anastomosing step.

12. The method of claim 11, wherein the anastomosing step and the arteriotomy creating step are each performed while the segment of the blood vessel is covered by a substantially intact portion of the epidermis of the body.

13. A method of implanting an end portion of a graft within a patient's body during a bypass grafting procedure, with the body including a circulatory system, comprising the steps of:

isolating a region of the area within the circulatory system from fluid communication with the rest of the area within the circulatory system to inhibit blood flow through a segment of a blood vessel located within the region, wherein the isolating step includes the step of inflating a plurality of balloons within the circulatory system to occlude blood flow within the circulatory system; and anastomosing the end portion of the graft to the segment of the blood vessel during the isolating step, wherein the blood vessel is an aorta, wherein the inflating step includes the step of inflating a first balloon of the plurality of balloons within the aorta to occlude blood flow at a first location in the aorta, wherein the inflating step further includes the step of inflating a second balloon of the plurality of balloons within the aorta to occlude blood flow at a second location in the aorta, wherein the first location is spaced apart from the second location, and further comprising the step of creating an arteriotomy in a sidewall of the segment of the aorta between the first location and the second location while (i) all of the plurality of balloons are inflated within the circulatory system, and (ii) prior to the anastomosing step.

14. A method of implanting an end portion of a graft within a patient's body during a bypass grafting procedure, with the body including a circulatory system, comprising the steps of:

isolating a region of the area within the circulatory system from fluid communication with the rest of the area within the circulatory system to inhibit blood flow through a segment of a blood vessel located within the region, wherein the isolating step includes the step of inflating a plurality of balloons within the circulatory system to occlude blood flow within the circulatory system; and anastomosing the end portion of the graft to the segment of the blood vessel during the isolating step, wherein the inflating step includes the step of inflating a first balloon of the plurality of balloons within the blood vessel to occlude blood flow at a first location in the blood vessel, wherein the inflating step further includes the step of inflating a second balloon of the plurality of balloons within the blood vessel to occlude blood flow at a second location in the blood vessel, wherein the first location is spaced apart from the second location, and further comprising the step of creating an arteriotomy in a sidewall of the segment of the blood vessel between the first location and the second location while (i) all of the plurality of balloons are inflated within the circulatory system, and (ii) prior to the anastomosing step.

15. A method of implanting an end portion of a graft within a patient's body during a bypass grafting procedure, with the body including a circulatory system, comprising the steps of:

isolating a region of the area within the circulatory system from fluid communication with the rest of the area within the circulatory system to inhibit blood flow through a segment of a blood vessel located within the region, wherein the isolating step includes the step of inflating a plurality of balloons within the circulatory system to occlude blood flow within the circulatory system; and anastomosing the end portion of the graft to the segment of the blood vessel during the isolating step, wherein (i) a first balloon of the plurality of balloons is included on a first distal portion of a first catheter, and (ii) a second balloon of the plurality of balloons is included on a second distal portion of a second catheter, and further comprising the step of:

advancing the first catheter and the second catheter within the circulatory system so as to position the first balloon and the second balloon within the circulatory system prior to the isolating step.

16. A method of securing an end portion of a graft to a blood vessel of a patient's circulatory system during a bypass grafting procedure, comprising the steps of:

preventing blood flow through a region of the circulatory system which includes a segment of the blood vessel by inflating a plurality of balloons within the circulatory system;

anastomosing the end portion of the graft to the segment of the blood vessel during the blood flow preventing step; and creating an arteriotomy in a sidewall of the segment of the blood vessel while (i) all of the plurality of balloons are inflated within the circulatory system, and (ii) prior to the anastomosing step.

17. The method of claim 16, wherein the anastomosing step and the arteriotomy creating step are each performed while the segment of the blood vessel is covered by a substantially intact portion of the epidermis of the body.

18. A method of securing an end portion of a graft to a blood vessel of a patient's circulatory system during a bypass grafting procedure, comprising the steps of:

preventing blood flow through a region of the circulatory system which includes a segment of the blood vessel by inflating a plurality of balloons within the circulatory system; and anastomosing the end portion of the graft to the segment of the blood vessel during the blood flow preventing step, wherein the blood vessel is an aorta, and wherein the blood flow preventing step includes the step of inflating a first balloon of the plurality of balloons within the aorta to occlude blood flow at a first location in the aorta, wherein the blood flow preventing step further includes the step of inflating a second balloon of the plurality of balloons within the aorta to occlude blood flow at a second location in the aorta, wherein the first location is spaced apart from the second location, and further comprising the step of creating an arteriotomy in a sidewall of the segment of the aorta between the first location and the second location while (i) all of the plurality of balloons are inflated within the circulatory system, and (ii) prior to the anastomosing step.

19. A method of securing an end portion of a graft to a blood vessel of a patient's circulatory system during a bypass grafting procedure, comprising the steps of:

preventing blood flow through a region of the circulatory system which includes a segment of the blood vessel by inflating a plurality of balloons within the circulatory system; and anastomosing the end portion of the graft to the segment of the blood vessel during the blood flow preventing step, wherein the blood flow preventing step includes the step of inflating a first balloon of the plurality of balloons within the blood vessel to occlude blood flow at a first location in the blood vessel, wherein the blood flow preventing step further includes the step of inflating a second balloon of the plurality of balloons within the blood vessel to occlude blood flow at a second location in the blood vessel, wherein the first location is spaced apart from the second location, and further comprising the step of creating an arteriotomy in a sidewall of the segment of the blood vessel between the first location and the second location while (i) all of the plurality of balloons are inflated within the circulatory system, and (ii) prior to the anastomosing step.

20. A method of securing an end portion of a graft to a blood vessel of a patient's circulatory system during a bypass grafting procedure, comprising the steps of:

preventing blood flow through a region of the circulatory system which includes a segment of the blood vessel by inflating a plurality of balloons within the circulatory system; and anastomosing the end portion of the graft to the segment of the blood vessel during the blood flow preventing step, wherein (i) a first balloon of the plurality of balloons is included on a first distal portion of a first catheter, and (ii) a second balloon of the plurality of balloons is included on a second distal portion of a second catheter, and further comprising the step of:

advancing the first catheter and the second catheter within the circulatory system so as to position the first balloon and the second balloon within the circulatory system prior to the blood flow preventing step.

21. A method of securing an end portion of a graft to a blood vessel, comprising the steps of:

inflating a balloon within the blood vessel so that the balloon partitions the blood vessel into a first vessel segment of the blood vessel and a second vessel segment of the blood vessel, wherein a flow of blood within the first vessel segment is prevented from advancing to the second vessel segment while the balloon is inflated within the blood vessel;

anastomosing the end portion of the graft to the second vessel segment while the balloon is inflated within the blood vessel; and creating an arteriotomy in a sidewall of the second vessel segment while (i) the balloon is inflated within the circulatory system, and (ii) prior to the anastomosing step.

22. The method of claim 21, wherein the anastomosing step and the arteriotomy creating step are each performed while the second vessel segment is covered by a substantially intact portion of the epidermis of the body.

23. A method of securing an end portion of a graft to a blood vessel of a circulatory system, comprising the steps of:

inflating a balloon within the circulatory system so that the balloon partitions the circulatory system into a first circulatory region and a second circulatory region, wherein a flow of blood within the first circulatory region is prevented from advancing to the second circulatory region while the balloon is inflated within the circulatory system;

anastomosing the end portion of the graft to the blood vessel while the balloon is inflated within the circulatory system, wherein the blood vessel is located within the second circulatory region; and creating an arteriotomy in a sidewall of a segment of the blood vessel while (i) the balloon is inflated within the circulatory system, and (ii) prior to the anastomosing step.

24. The method of claim 23, wherein the anastomosing step and the arteriotomy creating step are each performed while the segment of the blood vessel is covered by a substantially intact portion of the epidermis of the body.

25. A method of securing an end portion of a graft to a circulatory system, comprising the steps of:

inflating a balloon within the circulatory system so that the balloon partitions the circulatory system into a first circulatory region and a second circulatory region, wherein a flow of blood within the first circulatory region is prevented from advancing to the second circulatory region while the balloon is inflated within the circulatory system;

creating an arteriotomy in a sidewall of a segment of a blood vessel located within the second circulatory region while the balloon is inflated within the circulatory system; and anastomosing the end portion of the graft to the segment of the blood vessel while the balloon is inflated within the circulatory system.

wherein the anastomosing step and the arteriotomy creating step are each performed while the segment of the blood vessel is covered by a substantially intact portion of the epidermis of the body.

26. A method of securing an end portion of a graft to a blood vessel of a circulatory system, comprising the steps of:

inflating a balloon within the circulatory system so that the balloon creates a partition between a first circulatory region and a second circulatory region, wherein a flow of blood within the first circulatory region is inhibited from advancing to the second circulatory region while the balloon is inflated within the circulatory system;

anastomosing the end portion of the graft to the blood vessel while the balloon is inflated within the circulatory system, wherein the blood vessel is located within the second circulatory region; and creating an arteriotomy in a sidewall of a segment of the blood vessel while (i) the balloon is inflated within the circulatory system, and (ii) prior to the anastomosing step.

27. The method of claim 26, wherein the anastomosing step and the arteriotomy creating step are each performed while the segment of the blood vessel is covered by a substantially intact portion of the epidermis of the body.

* * * * *